United States Patent [19]

Brothers et al.

[11] Patent Number: 4,659,435

[45] Date of Patent: Apr. 21, 1987

[54] INTEGRALLY HEATED ELECTROCHEMICAL CELL METHOD AND APPARATUS

[75] Inventors: Jack A. Brothers, Painted Post; William T. Kane, Big Flats; Harold A. Brouneus, Painted Post, all of N.Y.; Margaret M. Layton, Raleigh, N.C.; Paul L. Walsh, Elmira, N.Y.

[73] Assignee: Corning Glass Works, Corning, N.Y.

[21] Appl. No.: 764,234

[22] Filed: Aug. 9, 1985

Related U.S. Application Data

[63] Continuation of Ser. No. 467,812, Feb. 18, 1983, abandoned, Ser. No. 488,094, Apr. 25, 1983, abandoned, and Ser. No. 488,371, Apr. 25, 1983.

[51] Int. Cl.[4] .......................................... G01N 27/58
[52] U.S. Cl. ............................... 204/1 T; 204/274; 204/406; 204/425; 204/426; 204/427
[58] Field of Search ............... 204/406, 408, 412, 424, 204/425, 426, 427, 428, 429, 274, 262, 1 S

[56] References Cited

U.S. PATENT DOCUMENTS

| | | | |
|---|---|---|---|
| Re. 28,792 | 4/1976 | Ruka et al. | 204/1 T |
| 3,514,377 | 5/1970 | Spacil et al. | 204/1 T |
| 3,546,086 | 12/1970 | Sayles | 204/408 |
| 3,869,370 | 3/1975 | Sayles | 204/1 T |
| 3,883,408 | 5/1975 | Kim et al. | 204/424 |
| 3,928,161 | 12/1975 | McIntyre et al. | 204/428 |
| 4,071,817 | 1/1978 | Bahl | 204/1 S X |
| 4,098,650 | 7/1978 | Sayles | 204/1 T |
| 4,251,342 | 2/1981 | Habdas et al. | 204/427 |
| 4,282,078 | 8/1981 | Chamberland et al. | 204/412 |
| 4,283,261 | 8/1981 | Maurer et al. | 204/408 |
| 4,407,704 | 10/1983 | Mase et al. | 204/1 T |
| 4,500,412 | 2/1985 | Takahashi et al. | 204/425 |
| 4,505,783 | 3/1985 | Mase et al. | 204/1 T |
| 4,505,790 | 3/1985 | Mase et al. | 204/130 |
| 4,505,802 | 3/1985 | Mase et al. | 204/425 |
| 4,505,803 | 3/1985 | Mase et al. | 204/425 |
| 4,505,804 | 3/1985 | Mase et al. | 204/425 |
| 4,505,805 | 3/1985 | Mase et al. | 204/425 |
| 4,541,900 | 9/1985 | Mase et al. | 204/1 T |

FOREIGN PATENT DOCUMENTS

| | | | |
|---|---|---|---|
| 0030164 | 6/1981 | European Pat. Off. | 204/412 |
| 0066851 | 12/1982 | European Pat. Off. | 204/406 |
| 0067437 | 12/1982 | European Pat. Off. | 204/406 |
| 3127472 | 1/1983 | Fed. Rep. of Germany | 204/427 |
| 1523550 | 9/1978 | United Kingdom | 204/425 |

OTHER PUBLICATIONS

R. Sproule, Zircoa News Focus, "Solid Electrolytes-New Applications for $ZRO_2$" (1970).

Primary Examiner—G. L. Kaplan
Attorney, Agent, or Firm—R. N. Wardell; J. Jamieson, Jr.; J. F. Posillico

[57] ABSTRACT

A novel electrochemical cell including a solid electrolyte heated to an elevated temperature for operation and an integral cell electrode/heater for heating the electrolyte. Solid electrolyte embodiments are described. The integral electrode/heater is applied to a surface of the solid electrolyte and is resistively heated by an alternating electric current. A portion of the solid electrolyte may also be resistively heated. The described or comparable cells may be incorporated into an oxygen detector or similar apparatus where the apparatus is operated by alternately heating the cell and measuring the emf developed by the cell across its electrode.

The invention is also, in part, a unique, solid electrolyte-integral cell electrode/heater configuration which provides a zone of uniform maximum heating at a predetermined location within the electrolyte and which, when used with a suitable resistive heating electric current, confines the current to the integral electrode/heater prolonging cell life. Another aspect of the invention is the use of a radio frequency alternating electric current for resistively heating an electrochemical cell. Preferably, the radio frequency selected is sufficiently high so as to eliminate any offsets in the emf developed by the cell which are caused by the heater current. The invention also includes an apparatus for measuring the concentration of particular gases, such as oxygen, incorporating either and, preferably, both other inventive aspects of the invention. The preferred cell configuration reduces the complexity of such an apparatus by eliminating the auxiliary heat source and provides a more accurate and reliable electrochemical sensing cell. Radio frequency heating allows the operations of cell heating and emf measurement to proceed independent and concurrently and provides a continuously responding, self-heating detection apparatus.

90 Claims, 13 Drawing Figures

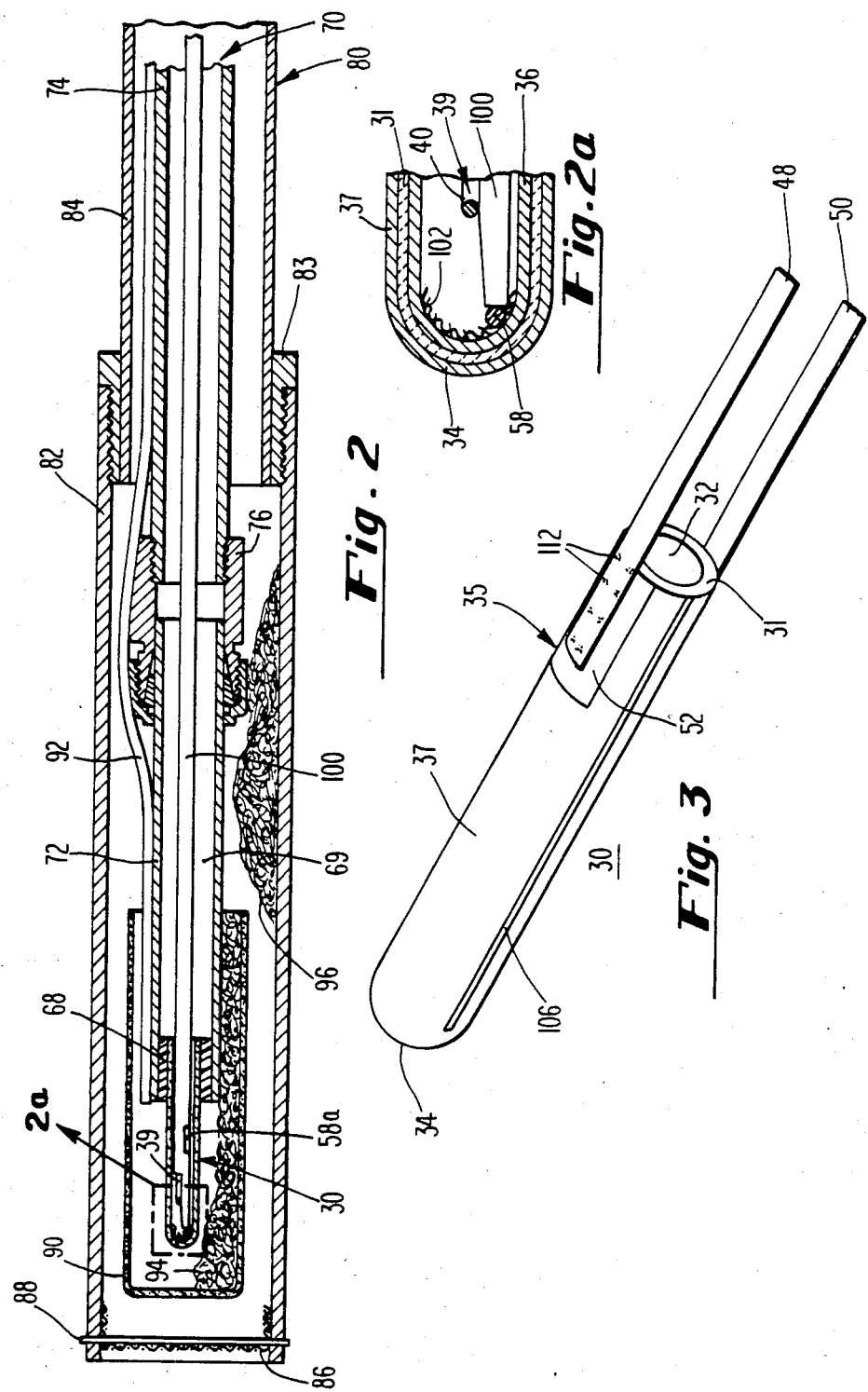

INTEGRALLY HEATED ELECTROCHEMICAL CELL METHOD AND APPARATUS

This is a continuation of application Ser. No. 467,812 filed Feb. 18, 1983 and of application Ser. No. 488,094 filed Apr. 25, 1983, both now abandoned, and of copending application Ser. No. 488,371 filed Apr. 25, 1983.

FIELD OF THE INVENTION

The invention relates to electrochemical cells operated at elevated temperatures and, in particular, to method and apparatus for heating electrochemical cells such as those used for detecting and/or measuring the concentration of oxygen or other gaseous compounds to an elevated temperature for proper operation.

BACKGROUND OF THE INVENTION

The use of electrochemical cells with solid electrolytic elements and gas porous platinum electrodes for detecting or measuring the content of oxygen or certain other gaseous compounds in a sample gas is well known. See, for example, U.S. Pat. No. 3,928,161 to McIntyre et al. and U.S. Pat. No. 4,282,078 to Chamberland et al. Materials such as zirconia and yttria-thoria are good oxygen ion conductors at elevated temperatures but are less ionically conductive or essentially ionically non-conductive at temperatures between the elevated temperatures and room temperature. Where the electrodes of such a cell are subjected simultaneously to differing oxygen concentrations, an emf is developed across the cell between the electrodes the value of which can be determined by the Nernst equation as follows:

$$emf = \frac{RT}{4F} \ln \frac{P_1 (O_2)}{P_2 (O_2)} + C$$

where
  emf = sensor output in volts
  T = absolute temperature
  R = gas constant
  F = Farraday constant
  $P_1 (O_2)$ = reference gas (oxygen) partial pressure
  $P_2 (O_2)$ = sample gas (oxygen) partial pressure
  C = cell constant Similar equations can be developed for other electrochemical systems. The cell constant C is a correction factor which reflects the inability of a particular cell to perform to theoretical limits represented by the preceding term of the equation. Cells used for oxygen concentration determination should be designed so as to consistently exhibit a known, predetermined cell constant value under all operating conditions in order that the bias in emf might be corrected or, preferably, eliminate such bias entirely (and thus the constant C).

A particularly useful application of oxygen concentration measuring apparatus is for the measurement of the oxygen content of exhaust gases from boilers, furnaces, glass furnaces, etc. in order that the combustion or smelting process may be optimally controlled. Closed loop oxygen sensing systems for combustion control in large steam plants used for power generation or industrial heating have been commercially available for at least ten years. Many of the systems available use a zirconia ($ZrO_2$) based solid electrolyte sensing cell installed in either an in situ or extractive mode. An in situ sensor is physically located within the boiler exhaust gas stream. Extractive systems are located outside the stack and require "plumbing" to carry a representative sample of the flue gas from the stack to the sensor. Currently available commercial units of both designs typically are provided with an auxiliary electric furnace to heat the sensor cell to a satisfactory operating temperature. In in situ sensors, the outer surface of the furnace also typically acts to protect the sensor probe from damage due to the high velocity particles in the flue gas and from dust caking which would affect the accuracy of the sensor The auxiliary electric furnaces used by currently available oxygen measuring systems have certain undesirable characteristics. They are an added component to the system and represent a significant fraction of its total cost. They are cumbersome to mount around the electrochemical sensor cell and require considerable design work to assure providing proper heating with simultaneous sample gas exchange They tend to be bulky and heavy, particularly when used with an in situ sensor which typically extends a meter or more into a flue or stack gas stream. Moreover, such furnaces consume substantial amounts of electrical power, typically between 200 and 400 watts, to maintain a sensor cell at a conventional 800° C. operating temperature. Lastly they are the least reliable component of the system and are a significant source of repair problems and cost.

Various attempts have been made to eliminate or at least reduce the size and complexity of the auxiliary furnace. For example, U.S. Pat. No. 4,098,650 to Sayles depicts an in situ oxygen measuring device in which the sensing cell is formed with a hollow interior into which is inserted a coil resistance wire heater. The aforesaid U.S. Pat. No. 3,928,161 to McIntyre et al. shows a different configuration for an in situ oxygen detector apparatus incorporating a resistance wire heater located within a tubular member supporting a disk shaped solid electrolyte sensor cell. U.S. Pat. No. 4,334,940 to Habdas et al. depicts yet another solid electrolyte oxygen sensor in which a resistance wire heater is incorporated internally into a tubular support member containing the solid electrolyte sensor cell. While these heater configurations would appear to use less power than auxiliary furnaces, the series resistance windings employed by each would continue to consume significant amounts of electrical power. Moreover, incorporating the heater windings as indicated requires additional manufacturing steps and increasing manufacturing complexity, particularly where the wires are to be threaded through fine holes. Lastly, heating of the solid electrolyte sensor cell would appear to be uneven and unpredictable. The sensor output is dependent upon temperature (see the Nernst equation, above) and failure to maintain the sensor at a specific temperature or to accurately measure the temperature of the sensor will lead to errors in the detector output.

OBJECTS OF THE INVENTION

Primary objects of the invention are to provide a novel apparatus and method for heating an electrochemical cell.

It is yet another object to simplify apparatus for heating a solid electrochemical cell.

It is yet another object of the invention to provide a novel electrochemical cell configuration for self-heating.

It is yet another object to provide a method of operating an electrochemical cell with integral heater/cell electrode as an accurate gas concentration measurement device.

It is yet another object to eliminate the necessity of an auxiliary furnace in gas concentration detection and other apparatus incorporating electrochemical cells which must be heated for operation.

Other objects of the invention include simplifying and providing a more reliable gas concentration measurement apparatus.

Yet another object is to reduce the electric power requirements for apparatus incorporating an electrochemical cell heated for operation.

It is a primary object of the invention to provide a highly reliable and accurate oxygen concentration measuring apparatus with a self-heating electrochemical cell sensor.

It is yet another object to provide a novel integral heater/cell electrode configuration for a solid electrochemical cell providing more uniform and controllable heating of the cell.

It is yet another object of the invention to provide a novel integral cell electrode/heater configuration for a solid electrochemical cell providing an enlarged area or zone of uniform heating of the electrolyte of the cell.

It is yet another object to provide an integral cell electrode/heater configuration for a solid electrochemical cell which diminishes the likelihood of a resistive heating current flowing through the solid electrolyte of the cell.

It is yet another object of the invention to provide an integral cell electrode/heater configuration for a solid electrochemical cell wherein adequate heating of the cell is provided by resistive heating of only the integral cell electrode/heater.

Still other objects are a novel method of and apparatus for resistively heating an electrochemical sensor of a solid state gas concentration sensing apparatus with an alternating electric current which minimizes or eliminates the effect of the alternating current on the magnitude of the emf developed by the sensor.

Further objects of the invention include a novel method of and apparatus for measuring the concentration of particlar gaseous substances using a solid electrochemical cell which is simultaneously, in a nonparallel fashion, resistively heated.

SUMMARY OF THE INVENTION

The aforesaid disadvantages of the prior art are overcome and the aforesaid and other objects achieved by the subject invention which in its most basic form, is an electrochemical cell incorporating an integral cell electrode/heater to heat the cell for operation. The cell was devised for incorporation into an oxygen sensing apparatus and develops an emf between two cell electrodes related to the concentration of oxygen in a sample gas directed against one of the electrodes.

While the preferred embodiment of the invention is an apparatus for generating an emf signal relating to oxygen concentration in a sample gas, the invention itself has much wider applicability. Similar solid state electrochemical cells are used to detect and measure other gaseous compounds such as oxides of carbon, nitrogen and sulfur, hydrogen sulfide and other gaseous substances to which some or all of the teachings of the present invention may be beneficially employed. Furthermore, it is believed there are applications beyond gas detection and/or measurement which can utilize a solid state electrochemical cell which must be heated for operation and for which the benefits of the present invention would be advantageous.

The basic invention is that of heating an electrochemical cell for operation by heating at least a portion of one of the two electrodes contacting the electrolyte. Accordingly, the broadest form of the basic invention is an electrochemical cell apparatus comprising a cell electrolyte and an integral cell electrode/heater contacting a portion of the electrolyte. According to an important feature of the invention, a current source is connected in a circuit across at least a portion of the integral cell electrode/heater for resistive heating. Preferably an electric current is supplied by the current source for resistive heating. Preferably too, suitable means, such as a switch for turning the current source off and on, is provided for varying the current circuited by the current source through the integral cell electrode/heater. In this way, the heating of the electrode and the temperature of the electrochemical cell may be controlled.

Preliminary work demonstrated that an integral heater/electrode can be formed on a solid electrolyte by the application of a layer or film of electrically conductive material to a surface of the solid electrolyte. For oxygen concentration detection apparatus, the preferred layer is formed from a material comprising platinum. For long-term reliability, the layer is preferably chemically bonded to the solid electrolyte. Platinum has been bonded to zirconia by mixing the platinum with a material which bonds to the zirconia. The solid electrolyte-integral heater/electrode configuration which has been examined and through which the invention has been successfully demonstrated comprises a tubular electrolyte element having an outer surface and opposing inner surface. The integral heater/electrode layer was applied covering a major portion of the electrolyte outer surface. This configuration minimizes heat loss and the development of undesired thermal gradients in the electrolyte.

The basic invention also includes the method of heating an electrolyte of an electrochemical cell to an elevated cell operating temperature by resistively heating one of the two cell electrodes contacting the electrolyte. According to the invention, the resistive heating step is accomplished by circuiting an alternating electric current through the cell. Preferably, the alternating current is circulated through only one of the two electrodes. Either description distinguishes the subject invention from the typical self-heating of a galvanic-type electric cell in generating a direct electric current where the same current circuits through the two electrodes of such a cell. Of course, separate independent alternating currents may be circuited through each of the two electrodes for faster cell heating. The subject invention further includes the step of simultaneously resistively heating at least a portion of the solid electrolyte, although this step is omitted in the preferred embodiment.

The utility of the basic invention was first demonstrated in a solid state gas detector for detecting and measuring oxygen content of a sample gas. In terms of the subject invention, such an apparatus comprises, in its simplest form, an electrochemical cell having a solid electrolyte exhibiting, when heated, an increased conductivity to ions of a predetermined gaseous substance to be identified (oxygen in the preferred embodiment); a first porous electrode contacting the electrolyte at a first location and forming with the sample gas a gas electrode; and a second, reference electrode contacting the solid electrolyte at a second location for generating a known, predetermined potential with the solid electrolyte. The electrochemical cell thus defined develops an emf due to ionic conduction across the electrolyte, at ionic conduction temperature, between the two electrodes. The ionic emf is related to the concentration of the particular compound in the sample gas. The apparatus further includes an electronic current source connected in a circuit across one of the two electrodes for heating at least a portion of the solid electrolyte between the electrodes by resistively heating the one electrode. Again, according to the invention, the integral heater/electrode is formed, at least in part, by an electrically conductive layer contacting the electrolyte. Preferably too, the integral heater/electrode layer is chemically bonded with the solid electrolyte.

In a gas sensor configuration, the solid electrolyte is preferably formed in a hollow tubular shape having an outer tube surface and an opposing inner tube surface with the integral electrode/heater layer covering a major portion of the outer tube surface. The preferred apparatus is operated as a concentration difference detector. The first electrode layer on the outer tube surface is gas porous and a second electrode is formed by providing a second gas porous, electrically conductive layer to the inner tube surface opposite the outer tube surface contacting layer. A sample gas is directed against one of the two layers while a reference gas, having a known concentration of the particular gas to be detected is directed against the remaining layer. The described apparatus are oxygen sensors and utilize a stabilized zirconia solid substrate electrolyte. Air, having a known concentration of oxygen, is used as a reference gas. The preferred layers are formed from a major proportion by weight of platinum and a minor proportion by weight of a substance chemically bonding with the zirconia.

The original apparatus was operated by resistively heating one of the electrodes. It was found that when the electrolyte reached a certain temperature, it too became electrically conductive. After the electrolyte reached a sufficiently elevated temperature for operation, preferably a predetermined elevated temperature, the resistive heating step was halted and the emf developed between the two cell electrodes measured. The method of heating the electrolyte to a predetermined elevated temperature is preferred in order to simplify the circuitry converting the emf output of the cell into a calibrated indication of oxygen concentration. Alternatively, the cell might be heated by resistively heating the one electrode and terminating the resistive heating step when the electrolyte has reached at least a temperature at which it is suitably conductive. After halting the resistive heating step, the emf of the cell and actual temperature of the electrolyte may be measured and the sample gas oxygen content determined by Nernst equation or by appropriate circuitry known to the art for modifying the emf output to generate a signal related to the sample gas oxygen content. The one electrode is resistively heated by circuiting an alternating electric current therethrough. In the original apparatus, a portion of the current would eventually circuit across a portion of the electrolyte resistively heating it directly. However, no portion of the current circuited through the second electrode.

One important aspect of the invention is a novel solid electrochemical cell with integral cell electrode/heater which allows the cell to be heated by resistively heating only the integral electrode. The preferred electrochemical cell is formed by a solid electrolyte having a hollow tubular portion with an outer surface and opposing inner tubular surface. The cell further includes an integral cell electrode/heater layer which covers substantially all but a pair of substantially parallel, opposing, longitudinally extending strips of the outer tube surface of the electrolyte. Preferably, the tubular portion of the solid electrolyte has a substantially circular, cross-section with a uniform cross-sectional thickness. This allows substantially uniform heating of the electrolyte. Preferably too, the integral cell electrode/heater layer is also of a substantially uniform composition and thickness along at least a major portion of the outer tube surface so as to provide a uniform power density and uniform heating of the electrolyte.

The preferred cell is closed at one end by a hollow, substantially hemispherical portion of electrolyte integrally formed with the tubular portion at the one end. The hemispherical portion of the electrolyte has a convex outer surface and an opposing concave inner surface and the integral electrode/heater layer covers at least a major portion of the convex outer surface so as to minimize the amount of heat lost through the hemispherical tip of the cell. In the preferred cell configuration, the opposing strips of exposed electrolyte outer tube surface extend from the remaining open end of the tubular portion of the electrolyte along the tube portion of the electrolyte to the hemispherical portion. In the preferred cell, the integral layer covers the entire convex outer surface of the hemispherical portion of the electrolyte tube again to reduce heat loss through the tip and thereby minimize the generation of thermal gradients within the electrolyte.

The described apparatus is heated by passing an electric (i.e., electronic) current through at least a portion of the cell. In the preferred embodiment apparatus, an electric current is passed through a pair of leads in electrical contact with the electrode layer, each lead being electrically connected at the open end of the electrolyte with an end of one of the two halves of the layer formed by the division of the layer at that open end by opposing strips of exposed electrolyte tube surface. The integral layer preferably has a total maximum resistance at room temperature of about one-half ohm or less and thus a resistance less than or equal to that amount between the lead contact points.

When used as a gas concentration difference cell, the preferred embodiment further includes a second electrode layer contacting the inner tube surface of the electrolyte opposite the outer layer along and extending along at least a portion of the length of the tube exposed by the two opposing strips. In the preferred embodiment cell, the electrode layers are gas porous and are formed from a material which is more than one-half by weight of platinum and the solid electrolyte is of a material which is more than one-half by weight zirconia.

The preferred cell is unique in that it is the first configuration known in which an yttria stabilized zirconia solid electrolyte can be heated to an operating temperature of about 800° C. or more by resistively heating only one of the two cell electrodes and no more than negligibly resistively heating the electrolyte. In other cell designs using an yttria zirconia electrolyte, partial short circuiting of the cell heater current through the electrolyte and, on occasions, through the electrolyte and second cell electrode has typically if not invariably occurred. In the preferred embodiment, no more than a negligible portion of the heater current passes through the electrolyte. The preferred embodiment allows heating of the electrolyte to a maximum temperature in a zone extending through the electrolyte between the heater/electrode and a second opposing electrode and covering an area of at least several square centimers, the temperature of the electrolyte in the zone varying about 10° C. or less from the maximum temperature. Important to achieving the creation of such a zone is the supplying of a substantially uniform electric power density over a major proportion of the integral electrode/heater layer contacting the solid electrolyte surface. This is achievable, in part, by the design of the preferred embodiment which minimizes the likehood of short circuiting of the heater current through the electrolyte.

Other important aspects of the invention are a method of an apparatus for resistively heating an electrochemical cell in a manner so as to minimize or totally eliminate any effect of the heater current on the value of the emf developed by the cell. According to the invention, a radio frequency alternating current is generated by a suitable radio frequency alternating electric current source and is passed through at least a portion of the cell by suitable circuitry connecting the radio frequency alternating electric current source in a circuit through at least a portion of the cell for resistively heating at least a portion of a cell by the current. Preferably, the radio frequency alternating electric current source generates an alternating electric current with a frequency sufficiently high as to eliminate any offset in the magnitude of the emf generated by the electrochemical cell which is caused by the frequency of the alternating current. It appears that direct current and alternating currents having a low frequency of alternation disrupt the ionic equilibrium at the electrolyte/electrode interface of the cell. It has been discovered that by raising the frequency of the alternating current, this disruption of equilibrium can be reduced if not effectively eliminated. It further appears for the cells studies thus far, that low radio frequency range alternating currents (3,000 to 30,000 hertz), specifically in range between about 3,000 and 200,000 hertz, have proved to have a sufficiently high frequency as to totally eliminate any apparent effect of the alternating heater current on the emf developed by the cell. The particular minimum frequency required varies at least with electrode composition. A current having a frequency between about 30,000 and 100,000 hertz is preferred for ease of interfacing the current source with the cell.

The electrochemical cell is preferably operated at a predetermined temperature. To accomplish this, temperature sensing means such as a thermocouple is provided for generating a signal related to the temperature of the cell and a control circuit responsive to the temperature signal is provided for controlling the power level of the alternating current supplied through at least a portion of the cell. In the described preferred embodiment, cyclical on/off switching of the alternating current is used to modulate the power supplied to the cell.

Preferably too, the electrochemical cell includes an integral cell electrode/heater through which the radio frequency alternating current is circuited. Again, the preferred embodiment cell allows the circuiting of all or all but a negligible portion of the alternating current through the integral electrode/heater and avoids the circuiting of anything more than a negligible portion of the current through the electrolyte.

A significant aspect of the invention is the cell/electrode configuration and the manner in which the alternating current source is supplied to the cell so as to minimize the generation of excessive heat at the contact points where the current enters and exits the cell. Preferably, the cell includes a solid electrolyte material in a hollow tubular form having opposing inner and outer tube surfaces and a cell electrode (integral electrode/heater) is formed, at least in part, by an electrically conductive layer covering a major proportion of the outer tubular surface of the electrolyte. A pair of strips of exposed electrolyte outer tube surface extending along at least a portion of the tubular electrolyte, divide the electrode layer into two end portions beginning near one open end of the tubular portion of the electrolyte. The electrode layer is continuous where the two portions meet at the remaining end of the electrolyte. A pair of leads extend from the current source to each of the two end portions of the electrode layer near the one open end. This configuration connects substantially all of the electrode layer in a circuit with the current source. Preferably again, the total resistance of the cell electrode between the two lead contact points is about one-half ohm or less at room temperature.

Yet another important aspect of the invention is an oxygen concentration measurement apparatus incorporating either, and preferably both, the radio frequency heating feature and novel cell-electrode configuration of the invention. Radio frequency heating and/or the preferred cell configuration can be adapted to similar apparatus known and used for the detection and/or measurement of the concentration of other types of gaseous chemical substances. The basic apparatus comprises an electrochemical cell having a solid electrolyte exhibiting an increased conductivity to ions of the predetermined gaseous substance when heated. A first gas electrode at a first location on the surface of the solid electrolyte provides an interface between the sample gas and the cell. A second reference electrode contacting the solid electrolyte at a second location is provided for generating a known, predetermined potential with the electrolyte. The cell develops an emf between the two electrodes having a magnitude related to the concentration of the predetermined gaseous substance in the sample gas. The apparatus further comprises, in one basic form, an electric current source connected with a circuit across the cell for passing a radio frequency alternating electric current through a portion of the cell, resistively heating that portion of the cell. In the preferred apparatus, a pair of electrically conductive leads extend from different portions of one of the two electrodes to the electric current source so that the radio frequency alternating current may be passed through at least a portion of the one electrode. Preferably too, the apparatus is designed so that the radio frequency alternating current passes only through the one electrode of the cell. Again, the preferred sensor apparatus includes an electrochemical cell having a solid electrolyte formed, at least in part, by a hollow tube shape having an outer tubular surface and an opposing inner tubular surface. The one resistively heated electrode is preferably formed by an electrically conductive layer which is porous to the gaseous substance and covers substantially all but a pair of narrow longitudinally extending strips of the outer tube surface dividing the layer into two sections extending along the tube portion of the electrolyte. Again the tubular portion of the electrolyte is preferably substantially circular in cross-section with a substantially uniform cross-sectional thickness at each cross-section and the integral electrode/heater layer is of a substantially uniform composition and thickness along a major portion of the outer tube surface for uniform heating of the electrolyte. Preferably too, the electrolyte is formed with an integral, hollow and substantially hemispherical portion closing one open end of the tubular portion of the electrolyte, the hemispherical portion having opposing outer convex and inner concave surfaces. The layer covers at least a major portion of the outer convex surface so as to minimize the generation of temperature gradients within the electrolyte. In the preferred embodiment, the longitudinally extending strips of exposed outer tube surface of the electrolyte are parallel dividing the layer into equal end sections and extend from the remaining open end of the tube portion of the electrolyte to the hemispherical portion of the electrolyte. Moreover, the layer covers the entire outer convex surface of the hemispherical portion of the electrolyte further minimizing the generation of temperature differentials in the electrolyte.

In the preferred apparatus, a pair of electrically conductive leads extend from the current source to the one electrode layer and the one electrode further includes a pair of metal foil pads, each pad joining an end of one lead to an end of the electrode layer. This reduces the effective surface resistivity of the layer in the vicinity of the lead contact points reducing the generation of heat in that area and thereby minimizing the likelihood of shorting of the alternating current through the electrolyte in the vicinity of the lead contact points.

The preferred apparatus is operated as a concentration differencing cell and is provided with a second, gas porous, electrically conductive layer circumferentially covering a portion of the inner tube surface over an area extending opposite at least a portion of the tube surface exposed by the two opposing strips. The opposing strips define, to some extent, the active zone of the cell. To prevent emf offset, the second electrode layer must be positioned opposite the point of maximum temperature of the outer electrode. Again, the preferred oxygen sensing apparatus has an electrolyte formed from a material comprising a major portion by weight of zirconia and electrode layers formed from a material comprising a major proportion by weight platinum.

Other important aspects of the invention are the method of heating an electrochemical cell and the specific related method of operating a gas concentration detecting apparatus which generates a signal related to the concentration of a particular gas and which includes the steps of generating an alternating current having a radio frequency level of alternation and passing the current through at least a portion of the cell to resistively heat the cell. Preferably, the frequency is between about 30,000 to 100,000 hertz for simplifying the problem of connecting the cell to the current source. Preferably too, the frequency of the current is sufficiently high as to eliminate any offset in the magnitude of the emf developed by the electrochemical cell which is caused by the frequency of the current. Viewed in another way, the alternating current frequency is sufficiently high that the magnitude of the cell emf is unaffected by the further frequency increase. It is further preferred but not required that the alternating current be passed through one of the two cell electrodes of the cell while passing no more than a negligible portion of the current through the electrolyte. Control of the temperature of the electrochemical cell is accomplished during the generating and passing steps by the contemporaneous steps of sensing the temperature of the electrochemical cell and varying, during the generating step, the power of the alternating electric current in response to the temperature sensing step.

According to another important aspect of the invention, the generation of an alternating current having a frequency sufficiently high such that the magnitude of the emf developed by a gas sensor cell is substantially unaffected by the current frequency allows the output of the cell to be measured during the step of passing the alternating current through at least a portion of the cell. Thus, the invention further includes, during the heater current passing step, the steps of sensing the emf developed by the electrochemical cell and generating a signal related to the magnitude of the emf for indicating the concentration of the particular gas in the sample gas.

BRIEF DESCRIPTION OF THE DRAWINGS

FIG. 2 is a sectioned view of the apparatus depicting the in situ sensor probe assembly;

FIG. 2a is an expanded view of the probe assembly of FIG. 2 in the area 2a;

FIG. 3 is a view of the preferred embodiment solid electrochemical cell;

DETAILED DESCRIPTION OF THE INVENTION

PREFERRED OXYGEN DETECTOR

Figure 1:
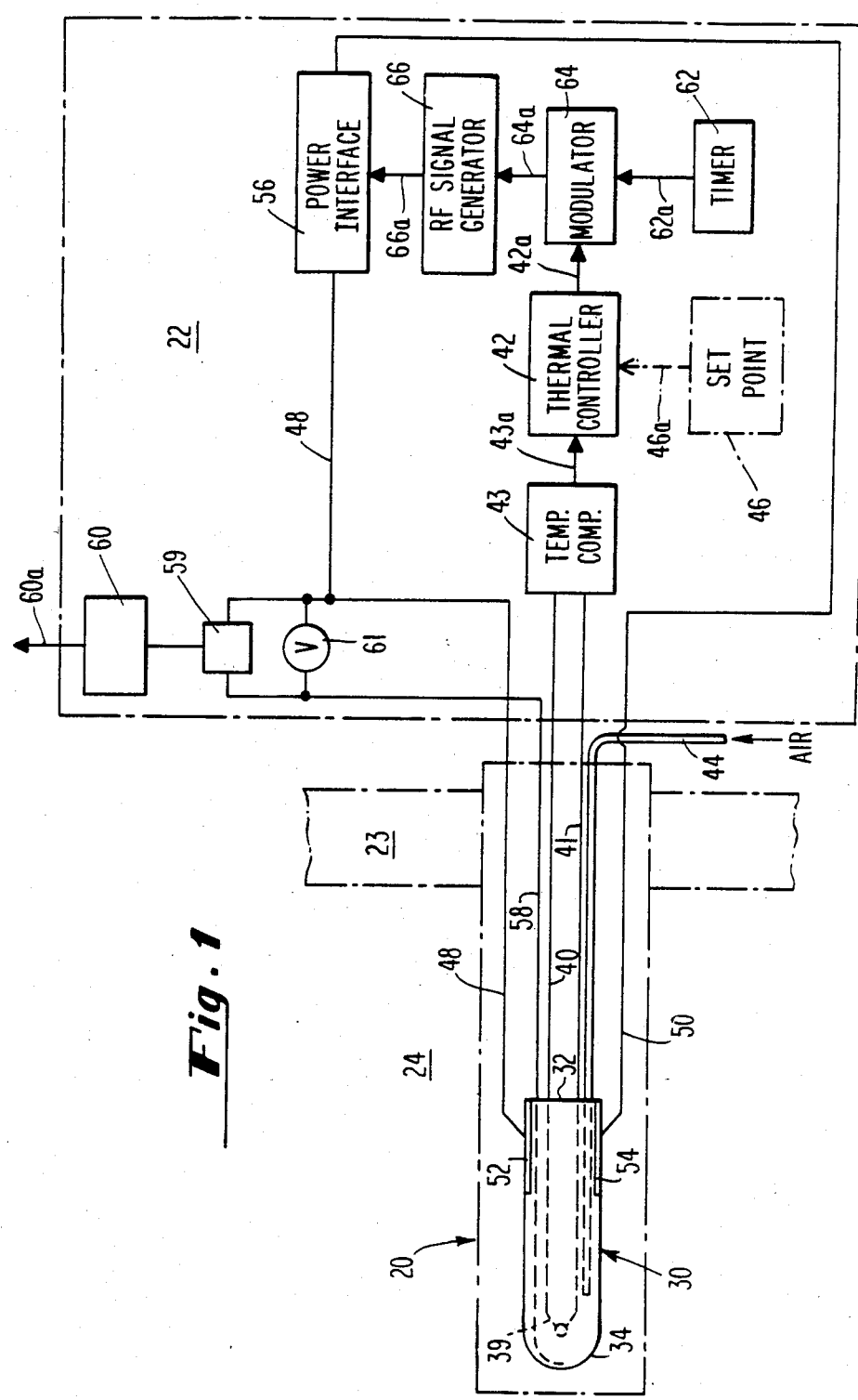
FIG. 1 is a schematic view of the preferred apparatus, in situ oxygen sensor incorporating a solid state electrochemical sensing cell with integral heater/electrode.

FIGS. 1 through 5 and 7 depict the components of the preferred embodiment of the present invention, a solid state, in situ, low temperature oxygen sensor for monitoring oxygen content in boiler stacks and the like. The apparatus is depicted schematically in FIG. 1 and includes a probe assembly 20, which is depicted in greater detail in FIG. 2 and is inserted through the wall 23 of boiler flue or chimney 24 into the combustion gas stream, and related electronics 22 depicted in greater detail in FIG. 7. The probe assembly 20 includes a tubular electrochemical sensor cell 30 together with protective and supporting elements further described in FIG. 2 to support and protect the electrochemical cell 30 in the flue 24. As is depicted in greater detail in FIGS. 3 through 5, the electrochemical cell 30 includes a solid electrolyte element 31 having a hollow tubular form with an open end 32 and an integral hemispherically formed closed end 4. The electrolyte tube 31 is a yttria (8% by weight) stabilized zirconia substrate fabricated by conventional ceramic forming techniques. As is better seen in FIGS. 4 and 5, an electrically conductive outer electrode layer 37 covers substantially all of the outer surface of the electrolyte element 31. A similar but separate layer 36 is provided on the inner surface of the electrolyte substrate 31 within the hemispherically closed half of the cell.

Returning to FIG. 1, a thermocouple 39 or other suitable temperature sensing device is provided within the electrochemical cell 30 for sensing the electrolyte temperature. Leads 40 and 41 carry an electrical signal generated by the thermocouple 39 to a temperature compensator 43. The compensator 43 develops a voltage level signal passed on line 43a to a thermal controller 42 which controls the heating of the cell 30 by controlling the amount of electrical current circuited through the outer electrode layer 37. The outer electrode layer 37 is used as a sample gas electrode and is exposed to the gases within the flue 24. The inner electrode layer 36 is used as a reference gas electrode and is supplied with ambient (outside) air, having a known concentration (20.95%) of oxygen, by a supply tube 44 or other appropriate means. A pair of pure nickel bus leads 48 and 50 are attached by means of pure platinum foil pads 52 and 54, respectively, to the outer electrode layer 37 and connect the outer electrode layer 37 across a power interface circuit 56. The power interface circuit 56 passes or circuits a radio frequency alternating electric current through the leads 48 and 50, pads 52 and 54, and outer electrode layer 37, thereby resistively heating the outer electrode layer 37 and raising the temperature of the covered solid electrolyte element 31 to an elevated level at which it becomes suitably conductive to oxygen ions. The layer 37, pads 52 and 54, and the portions of the leads 48 and 50 contacting the pads 52 and 54, respectively, together form the integral cell electrode/heater 35 of the subject invention. The inner electrode layer 36 is connected by means of yet another electrical lead 58 in a circuit with the outer electrode 37, foil pad 52 and lead 48 across a suitable electrical or electromechanical device for measuring or responding to the ionic emf of the cell 30 developed in the ionic conduction across heated electrolyte between the inner and outer electrode layers 36 and 37. For combustion control operations, the emf output of the cell 30 is preferably first amplified by a linear amplifier 59 and then converted to a signal linearly related to oxygen content of the gas in the flue 24 by a logarithmic amplifier 60. The output of the logarithmic amplifier 60 is passed via a line 60a to a conventional closed loop combustion process controller (not depicted), which forms no part of the present invention. Alternatively or in addition, the inner and outer electrode layers 36 and 37 may be circuited across a suitable measuring device such as a high impedance voltmeter 61 for a visual indication of oxygen concentration in the gases within the flue 24. The output of the cell 30, measured by the emf developed between the outer electrode layer 37 and inner electrode layer 36, is representative of the difference in oxygen concentration between ambient air and the gases within the flue 24. The apparatus may be configured for operation at a fixed cell temperature or, if desired, the thermal controller 42 may be provided with a set point input to control the operating temperature of the electrochemical cell. Completing the apparatus in FIG. 1 are a timer circuit 62, a modulator circuit 64 and a radio frequency signal generator 66 which together controllably supply a radio frequency digital signal to the power interface 56 which converts the digital signal to a similar frequency, low-voltage alternating current.

Operation of the FIG. 1 apparatus is as follows. The yttria stabilized zirconia electrolyte 31 of the sensor cell 30 exhibits an extremely low oxygen ion conductivity until it is heated above a temperature of about 600° C. A voltage difference signal from the thermocouple 39, indicating the maximum temperature of the electrolyte, is passed via leads 40 and 41 to the temperature compensator circuit 43 which compensates the thermocouple signal for the effect of connecting the leads 40 and 41 to the circuit elements 22. The compensated signal is amplified to a magnitude such that it equals the voltage level signal outputted by the set power circuit 46 along line 46a for an equal temperature. The amplified compensated thermocouple voltage level signal is outputted along line 43a to the thermal controller. The thermal controller 42, timer circuit 62 and modulator circuit 64 control the on-off cycling of the radio frequency signal generator 66. As presently embodied, the timer circuit 62 generates a digital timing pulse every 7 milliseconds on line 62a. The modulator circuit 64 responds to the pulse and switches the high frequency signal source 66 on for a fraction of the 7 millisecond period. The radio frequency signal generator 66 can be activated between 12½% and 97% of the 7 millisecond timing cycle. The duration of a high level signal outputted on the line 64a for activating generator 66 is controlled by the magnitude of the voltage level signal outputted by the thermal controller on line 42a. The radio frequency signal generator 66 outputs on line 66a, in the described embodiment, a 50 kilohertz square wave signal fluctuating between 0 and 15 volts. The square wave signal is converted by suitable circuitry in the power interface circuit 56 to a low voltage level (nominal +6 volts to −6 volts), alternating square wave current of the same frequency. Leads 48 and 50 circuit the high frequency alternating current generated by the power interface circuit 56 through the outer electrode layer 37. It will be appreciated that as the electrolyte 31 exhibits a relatively low electrical conductivity at or below the operating temperature of the sensor 30, which is about 800° C., that there is no flow or at most a negligible flow of alternating current through the electrolyte 31 or inner electrode layer 36 in the preferred embodiment at the indicated voltage levels.

Referring now to FIG. 2, the probe assembly 20 of FIG. 1 is depicted in a side-sectioned view. The major purpose of the probe assembly 20 is to support and extend the electrochemical sensor cell 30 sufficiently far into the stack 24 to obtain a good reading while protecting the cell 30 from abrasive particles in the stack gases and cooling from the stack gas flow. The electrochemical sensor cell 30 is affixed by suitable means, such as by a layer 68 of an electrically insulative ceramic cement, within the bore 69 of an extension tube 70. The tube 70 consists of an electrically insulative alumina tube section 72 of a convenient length so as to allow disassembly of the probe assembly 20 and the removal and/or replacement of the cell 30. The alumina tube section 72 is connected to a second extension tube section 74 of stainless steel or other suitable material by a Parker coupling 76 or other suitable means. The cell 30 and extension tube sections 72 and 74 are encased in a protective outer tube 80, formed in a preferred embodiment by lengths of stainless steel tubing 82 and 84 joined by a threaded coupling 83 welded to tube section 84. A wire mesh screen 86 is provided at the open end of the tube 80 to admit stack gases and to retain an insulative material 96, only a portion of which is depicted. The screen 86 is held in position by appropriate means such as pins 88, one of which is depicted in FIG. 2. The present embodiment of the preferred oxygen sensor also presently includes a gas porous ceramic cup 90 surrounding the cell 30 and proximal tip of the alumina extension tube section 72. A hollow tube 92, typically of stainless steel or other suitably heat and corrosion resistant material, is also currently provided with the cup 90 for sensor calibration purposes. The tube 92 carries gas mixtures having a known oxygen content, such as air, to the interior of the thimble 90 and outer electrode layer 37 of the cell 30. In this way, in situ calibration of the apparatus can be accomplished. The space between the thimble 90, sensor 30 and extension tube 72 is filled with an appropriate electrically and thermally insulative material 94 such a alumina silicate only a portion of which is illustrated in FIG. 2 for purposes of clarity. Similarly, the space between the porous ceramic cup 90 and extension tube 70, section tube 72, coupling 76, and metal tube section 74, and the outer stainless steel protective tube 82 is also filled with a gas porous, thermally and electrically insulative material 96, again such as alumina silicate and again only a portion of which is illustrated in FIG. 2 for clarity. The screen 86, outer insulation 96, porous ceramic cup 90 and inner insulation 94 are all gas porous allowing stack gases to reach the outer electrode layer 37 (see FIGS. 3-5) of the sensor cell 30. These elements also filter solid particulates from the stack gases entering the probe 20.

Inserted into the hollow interior of the cell 30 is a four bore alumina tube 100. Two bores of the tube 100 contains leads 40 and 41 forming the thermocouple 39 which is exposed, as indicated in FIG. 2, at the so-called 'active zone' of the sensor 31. That is the location where the solid electrolyte element 31 is heated to its maximum temperature by the outer electrode layer 37 acting as a resistive heater. A third bore of the alumina tube 100 acts as the air supply tube 44 carrying ambient air to the inner electrode layer 36 of the sensor cell 30. The fourth bore of the alumina tube 100 carried the lead 58 contacting the inner electrode layer 36 of the cell 30. FIG. 2a, an enlarged view of the area 2a of FIG. 2, shows one-half of the thermocouple 39, formed by the lead 40. Chromel-P ™ and Alumel ™ leads are used for a k-type thermocouple 39 and are joined where exposed from the four bore alumina tube 100. The inner electrode lead 58 has a pure platinum wire tip extending from the tube 100 which is joined within the tube 100 to a pure nickel wire at a point 58a in the vicinity of the junctions between the pure nickel bus leads 48 and 50 and the pure platinum pads 52 and 54, respectively. The purpose is to provide an inner electrode nickel-platinum junction which produces, at the sensor's operating temperature, a compensating emf that is essentially of equal magnitude and opposite polarity to that generated by the junction of the platinum foil pad 52 and nickel lead 48. The purpose is to minimize the magnitude of the cell constant, C, of the apparatus as well as to reduce construction costs of the apparatus. A fine platinum wire mesh 102 is positioned about the tip of the tube 100 so as to be compressed against the inner electrode layer 36 and lead 58 when the tube 100 is inserted into the cell 30. An electrical junction is thus formed between the inner electrode layer 36, platinum mesh 102 and inner electrode lead 58. Leads 48 and 50 from the outer electrode layer are not depicted in FIG. 2, but are covered, at least in part, by the cement layer 68 and extend down the bore 69 of the tube 70. An electrically insulative covering is provided as the leads 48 and 50 extend from the sensor 30 to prevent shorting or grounding.

While the preferred embodiment is an in situ oxygen sensor, the invention is not limited to in situ sensors or to in situ sensors having the indicated configuration. For example, the sensor 30 is easily adapted to an extractive mode. A sample gas may be supplied to the interior electrode layer 36 or exterior electrode layer 37, with air being supplied to the remaining electrode layer. Alternatively, the configuration of the in situ oxygen sensor 30 may be varied by inverting the orientation of the sensor cell 30 so that the cell 30 extends into and is protected by the alumina tube section 72. This would require modification to the positioning and configuration of the various electrode leads 48, 50, 58 as well as to the thermocouple 39. In this orientation, the inner electrode layer 36 would be used as the sample gas electrode while the outer electrode layer 37 would be exposed to ambient air and used as the reference gas electrode of the cell 30. Moreover, while an ambient air reference gas electrode is formed in the interior of the preferred embodiment cell 30, it is conceivable that a solid state reference electrode can be formed by using methods and materials known to the art eliminating the need to supply air to the cell 30 interior. See, for example, the solid, oxygen reference electrode revealed in U.S. Pat. No. 3,883,408 to Kim et al., incorporated by reference. It is further envisioned that the present invention may be usefully employed in other areas, particularly in the detection and measurement of other gaseous compounds, apparatus which typically employ similar solid state electrochemical cells 30 utilizing electrolyte and electrode materials selected for the gaseous compound to be detected. See, for example, U.S. Pat. No. 4,282,078 to Chamberland et al., incorporated by reference. It is further believed that at least some inventive aspects of the preferred embodiment oxygen detector apparatus may be usefully employed in the area oxygen and oxide concentration detection and measurement in fluids, such as molten metals.

PREFERRED ELECTROCHEMICAL CELL AND INTEGRAL ELECTRODE/HEATER

Figure 4:
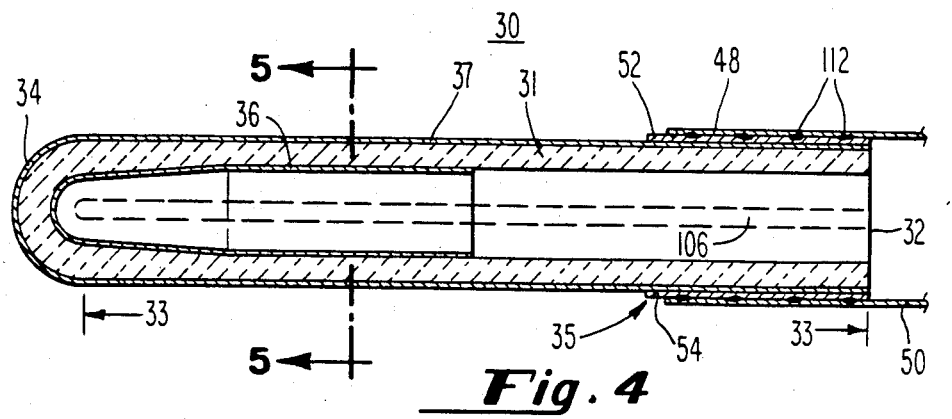
FIG. 4 is a lateral sectioned view of the cell in FIG. 3.
Figure 5:
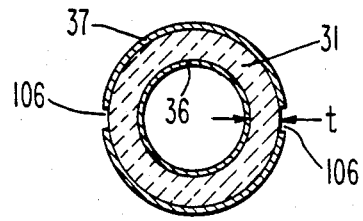
FIG. 5 is a cross-sectional view of the cell of FIG. 3 and FIG. 4 along the lines 5—5.

FIGS. 3-5 depict in greater detail the configuration and construction of the preferred embodiment electrochemical cell 30. The configuration of the cell 30 including the integral cell electrode/heater 35 comprising the outer electrically conductive, gas porous layer 37, pure platinum lead attachment pads 52 and 54 and the connected portions of pure nickel leads 48 and 50, are significant inventive aspects of the preferred embodiment. The emf developed by the cell 30 is controlled, in part, by the maximum temperature of the electrolyte 31.

This is the temperature T of the Nernst equation previously referred to. It has been observed that thermal gradients in the solid electrolyte 31 leading to differing maximum temperatures for the inner and outer electrode layers 36 and 37 cause an offset in the magnitude of the emf actually developed by the cell 30 from that predicted by the Nernst equation. The Nernst equation is only valid where the maximum temperature of the two electrodes are approximately equal. Furthermore, failure to locate and measure maximum temperature generated by the integral electrode/heater can lead to a runaway heating situation. In order to provide a reliable and accurate oxygen measuring apparatus, it is necessary to create an isothermal zone or enlarged area of maximum temperature extending substantially uniformly through and across the electrolyte (i.e., an "active region") between the electrode layers 36 and 37 at a known location. The creation of such a zone allows the temperature to be accurately determined and regulated and thermal gradients between the inner and outer electrodes to be minimized so as to reduce or eliminate a changing and unpredictable cell emf offset.

It has been discovered that the best manner to provide such an isothermal region in the electrolyte is to provide an integral heater/electrode covering a large surface area of the electrolyte 31 and a uniform power density. The preferred design minimizes the length to width ratio of the effective heater/electrode thereby minimizing total electrode resistance while still providing a substantially uniform power density over a large area of the electrolyte. A solid stabilized zirconia electrolyte 31 is provided in the shape of a hollow tubular section 33 and integral, hollow hemispherical section 34. The preferred embodiment sensor uses a partially yttria stabilized zirconia isopressed tubular substrate having a 38 mm overall length, 6 mm outer diameter and maximum inner diameter of 4 mm. The tubular portion 33 of the electrolyte 31 is preferably of a uniform circular cross-section, as is best seen in FIG. 5, and has a substantially uniform cross-sectional thickness, t, at each cross-section. The solid electrolyte tube 31 is formed by conventional ceramic techniques, preferably isopressing for greater dimensional accuracy and more consistent quality. The cross-sectional thickness, t, is substantially the same along most of the length of the tubular portion 33 of the electrolyte 31 but increases near the hemispherical end 34 as a result of the isopressing process. It is desirable to form the electrolyte 31 with as substantially a uniform thickness, t, throughout as possible for uniform heating. The preferred integral heater/electrode 35 is formed in part by the layer 37 of an oxygen porous, electrically conductive material applied to all but a pair of narrow diametrically opposing strips 106 of the outer surface of the electrolyte 31. A metallic (preferably platinum) based paste or ink composition is coated as uniformly as possible to the outer surface of the electrolyte 31 so at to form an electrode layer 37 of substantially uniform thickness and uniform electrical resistance. The coating is dried and, if appropriate, heated to sinter the electrode layer material to the electrolyte 31. An ink of the same material having a greater liquid content is used to "cement" the foil pads 52 and 54 to the electrode layer 37. Suitable means such as spot welds 112 are used to affix the leads 48 and 50 to the foil pads 52 and 54, respectively, before attachment of the pads to the electrode layer 37. The inner electrode layer 36 is formed by coating the inner surface of the electrolyte 31 with the same paste or ink.

Figure 6:
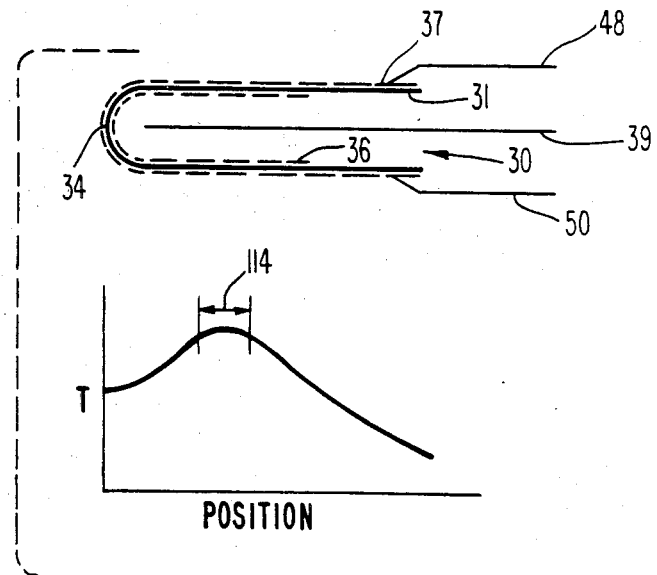
FIG. 6 depicts graphically the temperature within the cell of FIGS. 3-5 as a function of position from the closed end of the cell.

The outer electrode layer 37, being primarily metallic in all the embodiments being discussed, has a positive temperature coefficient of resistance, as do the metallic foil pads 52 and 54 and leads 48 and 50. Thus, the resistance of the electrode 35 increases with temperature. By employing a substantially uniformly thick outer electrode layer 37, a resistive heater having a substantially uniform power density is formed over the tubular portion 33 of the electrolyte 31. The metallic foil pads 52 and 54 effectively reduce the surface resistivity of the integral heater/electrode 35 near the open end 32 of the electrolyte tube 31. This reduces the electric power density and the resulting generation of heat in the vicinity of the pads 52 and 54. The strips 106 cause the alternating current supplied by the power interface 56 to travel along the length of the layer 37 and over the hemispherical end 34 of the electrolyte 31. At the operating temperature of the sensor 30 (about 800° C.), the outer electrode layer 37 acts as a black body radiator. The rate of heat loss through radiation from the outer electrode layer 37 is greatest at the hemispherical end 34 than along the length of the tubular portion 33 of the cell 30. Thus, the resistivity and power density of the electrode layer 37 is effectively reduced at that end 34. Maximum heating therefore occurs in the region between the hemispherical end 34 and the foil pads 52 and 54. FIG. 6 depicts diagrammatically the form of the sensor 30 and the resulting nominal temperature distribution through the electrolyte 31 as a function of position along the electrolyte length. In embodiments of the sensor 30 formed from zirconia tubes having an outer diameter of 6 millimeters, an inner diameter of 4 millimeters and a length of approximately 40 millimeters, an "active zone" 114 of maximum temperature having no more than about a 10° C. variation over about a 6 millimeter length of the electrolyte 31 can be generated beginning approximately 9 to 12 millimeters from the hemispherical tip 34.

In the depicted preferred embodiment of the cell 30, the strips 106 extend along the length of the outer surface of the electrolyte 31 from the open end 32 to the hemispherical portion 34. While it is not believed necessary to cover the entire hemispherical portion 34 with the electrode layer 37, as depicted, it is presently suggested to do so as it is believed that covering the entire surface of the hemispherical section 34 with the outer electrode layer 37 reduces heat conduction from the "active zone" to the tip 34 thus minimizing the thermal gradient in the "active zone". It also has the effect of distributing the current density over a broader area preventing the possible generation of hot spots at the ends of the strips 106 where the hemispherical portion 34 meets the tubular portion 33 of the electrolyte body 31. The strips 106 are no wider than is necessary to prevent shorting of the electrode layer 37 at the operating temperature of the sensor 30 and at voltage of the alternating current used to heat the outer electrode layer 37. For the preferred electrode layer material and an yttria stabilized zirconia electrolyte substrate 31 operated at a temperature of about 800° C. with an alternating current voltage fluctuating between about ±6 V, gaps approximately 0.76 millimeters wide in the circumferential direction of the electrolyte 31 were found to be suitable. Gaps 106 should be kept as narrow as possible in the circumferential direction to reduce thermal gradients developing due to electrolyte cooling in the unheated gaps 106.

The area of attachment of the bus strips 48 and 50 to the electrode layer 37 is a potential source of high electrical resistance and therefore of excessive and undesirable heat generation. For this reason and to reduce the overall power requirements of the cell 30, it is suggested that the resistance per unit length of the outer electrode 35 in the region of the intermediate foil pads 52 and 54 and bus strips 48 and 50 be kept to a value less than about 1/10th that in the "active zone". This is substantially achieved by the foil pads 52 and 54 bonded to the outer layer 37. If necessary, it is believed that further reduction in the resistance of the integral heater/electrode 35 can be achieved by overlaying the bus leads 48 and 50 with another layer of similar metal foil. Surface resistivity of the integral heater/electrode 35 and of the electrode layer 37 can be measured by the conventional four probe technique. The surface resistivity measurements reflect a changing resistance in the heater/electrode 35 and layer 37. The surface resistivity of the preferred embodiment platinum-bismuth trioxide electrode material is about 0.05 ohm/square (±50%) or less for a typical 0.001 inch film at room temperature and provides an electrode layer in the preferred apparatus having a total resistance of less than about one-half ohm at room temperature between the first and second nickel lead/platinum foil junctions (48/50 and 49/51). The test may also be used to determine the uniformity of the layer 37 as surface resistivity of the layer 37 is directly proportional to its thickness.

The depicted embodiment of the cell 30 with integral heater/cell electrode 35 is presently preferred for its superior performance given the present fabricating constraints. Other electrode layer application techniques are being studied which may provide a means for controllably varying the thickness of the electrode layer 37. When accomplished, this may allow variation in the construction of the integral heater electrode 35 such as the elimination of the foil pads 50 and 52, the expansion of the active region or the use of even smaller electrolyte shapes.

The proper functioning of the preferred embodiment cell results from the proper balancing of a number of interrelated factors including tube and heater layer size, shape, composition and electrical resistance/conductivity characteristics, sensor operating temperature and heating current voltage. Variation of any parameter may result in some significant portion of the heating current shorting through the electrolyte or the electrolyte and remaining electrode. This will necessarily affect the accuracy of the cell and will probably reduce its operating life.

Models of the preferred embodiment apparatus are presently being fabricated from yttria stabilized (8% by weight) zirconia substrate tubes which are readily available in the size and shape of the solid electrolyte element 31 being employed. However, suitable oxygen ion conducting solid electrolyte materials such as zirconia stabilized with other compounds and other oxides known in the art may be employed. Indeed, it has been observed that at the operating temperature of the cell 30 of approximately 800° C., that calcia stabilized zirconia is less electronically conductive than the yttria stabilized zirconia, a factor not deemed significant for the preferred embodiment of the cell and integral electrode/heater layer 37, but which may be important in other configurations to prevent a short circuiting of the alternating current through the solid electrolyte 31 during heating. For example, successful operation of a calcia stabilized zirconia electrolyte cell 30 has been demonstrated. At an operating temperature of approximately 800° C., the calcia stabilized zirconia is an order of magnitude less electrically conductive than the yttria stabilized zirconia. However, the calcia stabilized zirconia appears to be more susceptible to electrolytic decomposition from an alternating electric voltage than does the yttria material. The calcia stabilized electrolyte may be useful in a short operating life application and/or in a different electrode/electrolyte configuration where the reduced electrical conductivity of the calcia stabilized zirconia might prevent undesired shorting of the heater alternating electric current.

Electrode Material

Another inventive aspect of the preferred apparatus is the material employed for the electrode layers 36 and 37. The material has been found to be one of the key components affecting the accuracy, sensitivity and longevity of the sensor. The ideal material used has to be applicable in controllable thicknesses on the electrolyte 31, form a strong bond (preferably chemical) with the electrolyte to resist spalling or other forms of physical deterioration, have the same thermal coefficient of expansion or otherwise be sufficiently ductile in the thicknesses used to prevent spalling or cracking and have the appropriate electrical resistivity, preferably about 0.05 ohms/square or less again for a typical 0.001 inch thick film. For oxygen concentration sensing with the integral heater/electrode 35 the layer 37 is desirably permeable to gaseous oxygen. Because of its high catalytic activity for the oxygen equilibration reaction, platinum is a preferred oxygen detector electrode material. Nevertheless, platinum cannot be used alone as a heater material because it does not form a chemical bond to the zirconia substrate electrolyte 31 and, if resistively heated, will spall.

Initial experiments were performed using a previously known resistive heater material demonstrating a long-term physical stability with zirconia when heated. When dried, the material essentially comprised two parts by weight powdered platinum, one part by weight powdered gold and a small portion by weight of a glass ceramic frit binder. The material was applied as an ink by brushing or dipping to form a coating approximately 25 microns thick which consolidated to a film approximately 10 microns thick when dried and fired. However, to obtain a one-half ohm resistance desired for the integral heater/electrode 35, thicker films were required. These were formed by coating and then firing successive layers onto the electrolyte 31. The most uniform coating results were obtained by dipping the electrolyte tube into the ink, slowly withdrawing it at a uniform rate and then rotating the tube in a furnace while drying. The particular composition used was a number 2408 Hanovia paste consisting of two parts platinum, one part gold with 3.7% by weight Corning Glass Works #186 BED glass frit to which was added approximately 45% of a proprietary Hanovia liquid medium comprising essentially Texanol. The frit is a lead oxide, titania, silica glass which crystalizes to form $PbTiO_3$ at about 700° C. and which melts at about 1100° C. Three such coatings were applied to the outer and inner surfaces of a zirconia substrate tube. The substrate was dried and fired at approximately 900° C. for one hour after each coating. The electrode layer material was extremely adherent and could not be scraped off with a knife. The lead in the glass frit appeared to react with the gold and platinum to form a low melting temperature alloy chemically bonding the layer to the substrate but also acting as a gaseous oxygen block. The prototype sensor was slow to reach equilibrium and, accordingly, slow to respond to oxygen concentration changes. As other, more promising electrode materials were discovered, further experimentation with the glass frit based material was suspended. However, it is believed that some improvement in the oxygen permeability of the glass frit material might be achieved by a variation of the components. In particular, a reduction in the amount of glass frit used might be made to balance improved integral cell electrode/heater layer oxygen porosity with reduced adherability of the layer to the zirconia substrate. Scoring of the layer also improved oxygen permeability. The glass frit material performed adequately when used as an integral heater/reference electrode with a conventional platinum layer sensor electrode.

Initial experiments were directed in part to demonstrate that oxygen concentration could be measured using an electrode formed of this material. Although this proved to be true, the search continued for materials providing greater adhesion to the zirconia electrolyte substrate, lower resistivity and, in particular, greater gaseous oxygen permeability for quicker sensor response A preferred integral electrode/heater layer material has been discovered possessing these qualities. In addition, the new material is used to provide equal resistivity in thinner layers than the glass frit material thereby reducing costs. The preferred material paste is supplied by Engelhard Industries, Inc. and prepared by adding to their standard platinum sensor electrode paste, a small amount of bismuth trioxide. The paste is formed from a mixture of dry components comprising a major proportion by weight powdered platinum and a minor proportion by weight bismuth trioxide ($Bi_2O_3$). Trace amounts of gold (0.1–0.5% by weight) and other materials may be present. The dry components are mixed with a suitable liquid vehicle, again such as Texanol, to form a fluid mixture which can be applied to the zirconia substrate electrolyte 31 by a variety of methods. It was found that a coating approximately 0.001 inch thick (about 0.025 mm) provides an electrode layer 37 with an approximately one-half ohm or less total resistance at room temperature which could be heated to an operating temperature of about 800° C. with as little as 15 watts of energy. The paste appears to form a dark residual layer, which may be an alloy, on the substrate after firing. Electron microprobe analysis has shown that the layer forms a chemical bond at the zirconia interface and that the bismuth is concentrated at the interface. Moreover, the material exhibited extremely high gaseous oxygen permeability as indicated by virtually instantaneous response of test sensors to variations in oxygen concentrations in sample gases employed.

Bismuth trioxide is added in amounts sufficient to improve the adherence or bonding of the resulting electrode layer to the solid electrolyte. It is believed that bismuth trioxide in amounts of up to 10% by weight and preferably between about 1% and 5% by weight may be beneficially employed to form an oxygen porous integral heater/cell electrode layer. The bismuth trioxide appears to act as a flux, as does the gold. Thus, it is believed that the amounts of bismuth trioxide and gold may be varied from the indicated amounts, at least to some extent, without deleterious effect on the characteristics of the resulting layer. It is also suspected, but has not been verified to date, that the bismuth trioxide may be useful in forming electrode layers with base as well as noble metals, where base metals have heretofore been employed in the past. Moreover, the discovered composition may be advantageously employed as a gas electrode material where an integral heater/electrode application is not needed by virtue of its ability to chemically bond the preferred platinum electrode material to a zirconia substrate in an oxygen porous layer.

The preferred paste electrode material is presently being hand applied. A single application provides a layer approximately 0.001 inches (25 microns) thick after firing. Variations in the thickness of the outer electrode layer 37 of the preferred embodiment resulting from these application methods have been observed to produce a variation in surface resistivity of within about ±50% from an average value of about 0.05 ohms/square/mil or less at room temperature. This has proved to provide adequately uniform heating. In this regard, it is believed that the zirconia electrolyte substrate 31 acts as a heat sink diffusing heat rapidly away from hot spots in the electrode layer 37 resulting from uneven layer thickness. Before application of the electrode paste to the outer surface of the electrolyte tube 31, the surface was masked for the slots 106. After each application of the electrode paste, the coated electrolyte substrate was heat-treated at about 980° C.±15° C. for about 15 minutes to sinter the paste. Overfiring appears to reduce the oxygen permeability of the resulting layer. One coat formed the outer layer 37; three coats of the paste were applied to the inner surface of the electrolyte substrate 31 to form the inner electrode layer 36. The coated substrate was heat-treated as previously indicated between each application. Three coats were used to form the inner electrode layer 36 because of the difficulty of applying the paste to the tube interior and the desire to ensure continuity of the inner electrode layer over the inner surface of the electrolyte substrate 31.

Radio Frequency Heating

Other important inventive aspects of the preferred embodiment oxygen sensor and integral heater/electrode cell are the method and apparatus used to resistively heat the cell. It has been observed, in the course of the development of the preferred embodiment apparatus, that the magnitude of the emf developed by the electrochemical cell was affected by the relatively low frequency alternating current (conventional 60 Hz line current) initially used for resistively heating prototype cells. When not influenced by a strong electric or magnetic field, it is believed the oxygen ions in the solid zirconia electrolyte immediately adjacent each electrode layer 36 and 37 will be in equilibrium with the oxygen partial pressure in the gas adjacent the electrode layer 36 and 37 and that the existence of a strong electric or magnetic field will disturb that equilibrium. It was observed that when a steady, low frequency, sinusoidal electric current (i.e., conventional 60 hertz line current) was applied to the heater electrode layer, it was found impossible to simultaneously obtain a meaningful measure of the potential developed between the inner and outer electrodes. A digital type voltmeter, which is in essence a periodic sampling instrument, will read out a wide range of potential levels. An analog type voltmeter will read out a steady average potential which, however, is far different from the potential which would be produced by that sensor when heated isothermally by a separate heat source such as a conventional auxiliary electric furnace. The shift in the average sensor emf developed due to the low frequency electromagnetic field surrounding the integral heater/electrode is in that direction (i.e., more negative) which is indicative of a lowering of the partial pressure of oxygen adjacent that heater/electrode. On some of the earliest embodiment sensors, the 60 cycle current shifted the average emf by as much as about 225 millivolts. This necessitated following a repetitive heat first then measure cycle in using the early embodiments of the apparatus. It was discovered that as the frequency of the sinusoidal heating current is increased, the average value of the sensor potential shifts in the direction which is indicative of a more correct reading of the oxygen partial pressure at the heater/electrode. Above some sufficiently high frequency, the emf developed by the cell becomes stable and unaffected by the frequency of the heater current.

It has been observed in various embodiments of the subject oxygen sensing apparatus that the permeability of electrode/heater layer to oxygen has a bearing on the minimum frequency of the heater alternating current that can be employed. The platinum-gold-glass frit material initially employed exhibited a rather poor oxygen permeability. The minimum usable alternating frequency current was in the vicinity of 200 KHz. This is in what is conventionally understood to be the low frequency portion (30–300 KHz) portion of the radio frequency spectrum. It was found that with respect to the preferred platinum-bismuth trioxide electrode/heater layer material, the minimum usable frequency was below 10 KHz which lies within what is generally understood to be the very low frequency portion (3–30 KHz) of the radio frequency spectrum. For ease of coupling between the power source and electrode heater layer, it has been found preferable to employ a square wave alternating current in a range of about 30 KHz to 100 KHz. As previously indicated, the power interface circuit 56 of the preferred embodiment apparatus generates a 50 KHz square wave alternating current. Higher frequency alternating currents can be employed if power source switching losses are not excessive or interference with radio communication services does not pose a problem. Moreover, a sinusoidal alternating current may be employed in place of a square wave current. There is a significant amount of odd harmonic energy in square wave currents typically generated by existing equipment. Therefore, the fundamental frequency for a square wave current may be somewhat lower that that of a sinusoidal current to have an equivalent end effect on the observed electrochemical cell potential. As the cell developed emf can be made insensitive to the heater current by employing a sufficiently high frequency current, a variety of oxygen concentration apparatus operating methods can be employed. For example, the alternating heater current can be continuously circuited through the integral heater/electrode layer and its amplitude varied in order to provide the required heat input to maintain a stable electrolyte temperature. Alternatively, a constant amplitude alternating current may be switched on and off for variable lengths of time in order to supply the required heat input. In that scheme, which is incorporated into the preferred embodiment apparatus disclosed, the off-time interval is held short enough, for example about 50 milliseconds or less, that the transient temperature excursions in the active part of the sensor cell are below the levels which would produce unacceptable variations in the emf developed by the cell.

As an example of the performance capability of the preferred embodiment apparatus, the preferred embodiment electrochemical cell with platinum-bismuth trioxide electrode layers was configured in a heat and measure mode of operation where the instantaneous cell emf was interrogated by a sample and hold read out system immediately prior to the reapplication of each burst of radio frequency heater current. For a change in the off-interval period length from approximately 0.03 to 0.27 seconds, the change in the measured instantaneous potential for one typical experimental cell was in the worst instance 0.7 millivolts. Changing the partial pressure of the oxygen to the inner electrode from a level of 20.95% to 2.79% for cell operating nominal temperature 1073° K., the actual change in instantaneous potential developed by the experimental cell varied from 46.1 to 46.3 millivolts over the above indicated range of off-time interval lengths. According to the Nernst equation, such a concentration change at the indicated temperature should produce a theoretical change in the sensor potential of 46.5 millivolts. Over the same range of off-time interval lengths, the value of the potential observed with an average reading meter was essentially constant at 46.2 to 46.3 millivolts. Without correction, these numbers represent, in the worst case, an error in the determination of partial pressure of oxygen of less than about 2%.

Figure 7:
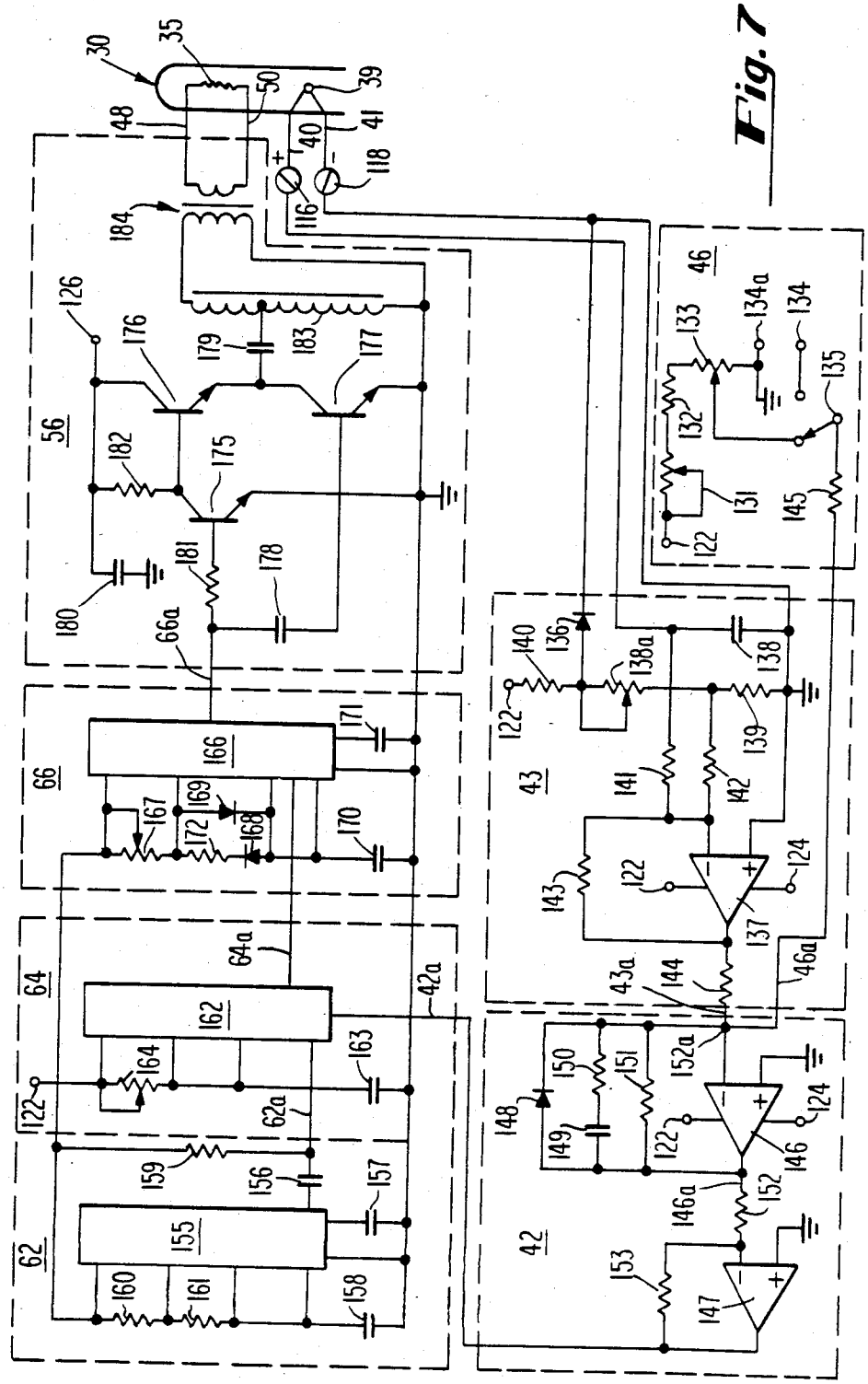
FIG. 7 depicts schematically the electrochemical cell temperature control circuitry of FIG. 1.

Referring now to FIG. 7, there is depicted in greater detail the components of the thermal controller 42, temperature compensator circuit 43, timer circuit 62, modulator circuit 64, high frequency signal source 66 and power interface 56 which together act as a closed loop temperature control circuit for the cell 30. The set point input circuit 46 is optionally provided in order to adjust the operating temperature of the cell 30. A suitable voltage level signal might otherwise be generated by another circuit element to represent a fixed operating temperature for the cell 30. The overall function of the circuit elements 42, 43, 46, 56 and 62 through 66 have been previously described.

As is indicated in FIG. 7, the set point circuit 46 includes a set point calibration circuit formed by a variable resistance 131 and fixed resistance 132. Also included in the circuit 46 are an operator controlled potentiometer 133 with temperature indicating control dial (not depicted) for operator selection of the cell operating temperature, automated set point input junctions 134 and 134a where an externally generated set point voltage signal may be inputted into the set point circuit 46 for automatic temperature control and a manually operated switch 135 for selecting operator or automatic set point control. The circuit 46 generates a voltage level signal passed on line 46a to the thermal controller circuit 42.

Also providing an input to that circuit 42 is the thermocouple temperature compensation circuit 43 which includes a cold junction compensation diode (type IN916) 136, operational amplifier (type OP07) 137, capacitor 138, variable resistor 138a and fixed resistors 139 through 143. Screwheads 116 and 118 represent a circuit junction block to which the thermocouple leads 40 and 41 are connected. The diode 136 is, in reality, located at the junction block so as to be at an identical temperature to that of the negative (Alumel TM) thermocouple lead 41. The operational amplifier 137 accepts at its negative input, the voltage level signal on the positive (Chromel TM) lead 40 of the thermocouple 39 and a temperature compensated voltage level derived from the cold compensation diode 136. These voltage level signals are summed together and amplified so that a compensating voltage due to change in room temperature emf at the termination of the input of the thermocouple 39 is added to the thermocouple signal thus restoring the reverse emf effect caused by connecting the thermocouple leads 40 and 41 to the room temperature junction block. Capacitor 138 is provided to decouple the thermocouple emf from any fluctuating emf component which might be induced in the thermocouple 39 by the alternating heater current. Variable resistor 138a provides means for adjusting the temperature compensation. The remaining resistors provide, with the other elements, an effective gain of 122. The amplified and compensated voltage of the thermocouple 39 is passed on line 43a to the thermal controller 42.

The thermal controller circuit 42 is formed by first and second operational amplifiers (type 347) 146 and 147 with related feedback circuits and resistors 144, 145 and 151 adjusting the gain of signals on lines 43a, 46a and 146a, respectively. The first operational amplifier 146 together with diode 148, capacitor 149 and resistances 150 and 151 form a novel combination deviation amplifier and two mode (percent proportional band and integral functions) controller. The room temperature compensated thermocouple voltage outputted on line 43a is combined with the set point voltage level signal outputted on lines 46a at junction 152 and the combined voltages, together with feedback voltage are fed into the negative input of the first operational amplifier 146. The set point circuit and temperature compensation circuit voltage level signals are scaled for 5 millivolts/°C. The set point voltage level signal is the opposite polarity of that outputted by the compensation circuit amplifier 137 so that the algebraic sum of the output of the compensator circuit 43 and set point circuit 46, as computed by the amplifier 146, is equal to the proportional deviation error selected for optimal temperature control loop stability and desired whole temperature accuracy. The resistors 151 and 144 provide a fixed proportional band error (1%) which represents the allowable percentage difference between the voltage levels on lines 46a and 43a. Reset action occurs as a function of error integration across the capacitor 149. The combination of proportionalizing and reset action is selected to provide, in the preferred embodiment being described, optimal loop stability and whole temperature accuracy within ±1° C. with expected oxygen sensor upsets. Diode 148 is provided to improve the response time of the two mode controller. The diode prevents the output of the amplifier 146 from rising much above zero, as would occur if there were a sudden call for a lower control temperature. The diode 148 reduces the integration requirement imposed on the capacitor 149 under such conditions allowing a faster return to control. The second operational amplifier 147 together with resistors 152 and 153 form a unity gain inverter which reverses the polarity of the output of the first amplifier 146 for driving the modulator circuit 64.

The timer circuit 62 and modulator circuit 64 are formed from a single integrated circuit timer element (type 556) together with related capacitors and resistances. The single integrated timer circuit is represented functionally by two separate timer elements 155 and 162 in FIG. 7. The timer circuit 62 is formed by the timer element 155 together with capacitors 156, 157, 158 and resistors 159, 160 and 161. Resistor 160 is connected between the first reset and discharge function of the integrated circuit timer while resistor 161 is connected between the first discharge and first threshold functions of the integrated circuit timer. Resistors 160 and 161 define the width (which is arbitrary) of the timing pulse outputted by the timer circuit 62. Capacitor 158 is provided between an input voltage source and the first trigger function of the integrated circuit timer and defines the time period (7 milliseconds in the described embodiment) between consecutive pulses outputted by the timer circuit 62. Capacitor 157 is provided to bypass the first control voltage function. Resistor 159 and capacitor 156 smooth and shape the signal outputted by the timer circuit 62 on the line 62a.

The output of the timer 62 is passed via the line 62a to the modulator circuit 64 which includes the second timer element 162, capacitor 163 and variable resistor 164. The timer element 162 is formed by suitably wiring (starting from upper left side of 162) the second reset, discharge, threshold, control voltage and output functions of the 556 integrated circuit timer. The capacitor 163 and variable resistor 164 determine the proportion of the 7 millisecond period for the output of the timer element 162 is high on line 64a. The resistor 164 is adjusted to provide for a maximum high output duration of 98% of the 7 millisecond pulse.

The timer element 155 is connected as a free running oscillator. The timer element 162 is connected in a monostable mode so as to be triggered by the negative going edge of each of the consecutive pulses from the timer element 155. The threshold triggering voltage of the timer element 162 is further modulated by the voltage level signal passed from the thermal controller circuit 42 along the line 42a. The timer circuit 162 thus configured acts as a pulse width modulated oscillator. With consecutive pulses being outputted by the timer element 155 at 7 millisecond intervals, the maximum pulse width of the high output level signal outputted by the timer element 162 is adjusted to 6.8 milliseconds by the variable resistor 164 with a threshold voltage of 12.5 supplied from the thermal controller circuit 42. The minimum stable pulse width supplied by the timer element 162 in the depicted configuration is one millisecond with a threshold voltage of 2 from the thermal controller 42. Thus, the total range of effective thermal controller control of the modulator circuit 64 is approximately between 12.5% and 97% of the 7 millisecond duty cycle. The on/off (high/low) voltage level signal outputted by the timer element 162 is passed via line 64a to the radio frequency signal generator circuit 66.

The circuit 66 is formed by an integrated circuit timer 166 (type 555), variable resistor 167, diodes 168 and 169, capacitors 170 and 171 and fixed resistance 172. The timer 166 is also wired as a free running oscillator generating a square wave output signal fluctuating between levels of about 0 and +15 volts at a frequency of 50 KHz. The output of the oscillator 162 is switched on and off by applying the width modulated pulses outputted by the modulator circuit 64 on line 64a to the reset function of the type 555 timer element 166. The frequency of the output of the timer circuit 166 is determined by the combination of capacitor 170 and resistors 167 and 172. The variable resistor 167 is connected between the power input (Vcc) and discharge functions of the 555 timer. The resistor 172 and diodes 168 and 169 are connected between the discharge and threshold functions of the timer while the line 64a feeds into the reset functions. Capacitor 171 by-passes the voltage control function. The variable resistor 167, fixed resistor 172 and diodes 168 and 169 are provided to cause the timer element 166 to generate a symmetrical square wave with equal on and off time periods. Actual adjustment is provided by variable resistor 167. Diodes 168 and 169 provide an alternative discharge path for voltage charge on capacitor 170 which itself is selected to determine the frequency of the signal (50 KHz) outputted on the line 66a. This assures that the signal generated by the signal generator 66 has an on time of less than or equal to 50% of the duty cycle. This is necessary in order to control symmetric AC heating current through a power interface circuit drive coupling capacitor 179.

The power interface circuit 56 is formed in the preferred embodiment by a novel charge-discharge square wave alternating current signal generator formed by a first transistor (type 2N2218) 175, second and third transistors (type 2N6284) 176 and 177, AC non-polarized capacitors (polyfilm) 178 and 179, electrolytic capacitor 180, and fixed resistor elements 181 and 182. The transistors 175, 176 and 177 form a drive circuit. The transistor 175 is an inverter the purpose of which is to provide a 180° phase inversion of the 50 KHz oscillator signal outputted by the radio frequency signal source 66, along with necessary current amplification to drive the transistor 176. The oscillator 166 drives the transistor 177 through the coupling capacitor 178. The action of driving transistors 176 and 177 alternately cause a direct current to flow through the transistor 176 into capacitor 179 and then to cause another direct current to flow from capacitor 179 and through transistor 177 to a common circuit return. Thus, the capacitor 179 is alternately charged by the transistor 176 and discharged through the transistor 177 at a frequency equal to that of the driving frequency (50 KHz) provided by the modulator 66. Capacitor 179 acts like an alternating current generator causing an alternating electric current to flow through the load comprising the transformers 183 and 184. Resistors 181 and 182 adjust the voltages passed to the base and collector, respectively, of transistor 175. Capacitor 180 provides a by-pass for a +45 volt power source fed into the power interface 56 at location 126. The drive coupling capacitor 179 decouples the DC component from the AC current generated by the transistors 176 and 177 causing an alternating square wave current fluctuating between about +20 and −20 volts to flow through the toroid auto transformer 183. The charge-discharge action of the capacitor 179, unlike the conventional push-pull configuration, requires only one power source supplied at the location 126. The circuit as configured outputs a maximum power of about 30 to 40 watts. The present drive circuit has the advantages of reduced cost, size and improved reliability over more complicated push-pull power circuits and is an improved device where a simple on/off square wave alternating current is needed. The toroid auto transformer 183 steps up the voltage passed to the conventional step-down (isolating toroidal) transformer 184 which, in turn, increases the current passed through the heater circuit 35 of the cell 30 from a level of about 1 amp to about 6 to 7 amps and reduces the voltage accordingly.

The depicted circuit utilizes three power sources: +15 volts denoted by junctions 122, −15 volts denoted by junction 124 and +45 volts denoted by junction 126. The following other circuit elements were used.

| Resistance | Element Resistors |
|---|---|
| 1 ohms | 139 |
| 200 ohms | 138 a (maximum) |
| 330 ohms | 182 |
| 1k ohms | 150 & 181 |
| 5k ohms | 131 (maximum) |
| 8.2k ohms | 141, 142 |
| 10k ohms | 133 (potentiometer), 140, 152, & 153 |
| 15k ohms | 159, 172 |
| 18k ohms | 132 |
| 20k ohms | 160 |
| 25k ohms | 167 (maximum) |
| 100k ohms | 144, 145, 161 & 164 (maximum) |
| 1 mega ohm | 143 |

| CAPACITORS | |
|---|---|
| Capacitance | Element |
| 1 microfarad | 178 |
| 10 microfarad | 138 & 179 |
| 100 microfarad | 180 |
| 0.001 farads | 149 & 170 |
| 0.0015 farads | 156 |
| 0.1 farad | 157, 158, 163 & 171 |

ALTERNATE EMBODIMENTS

Figure 8:
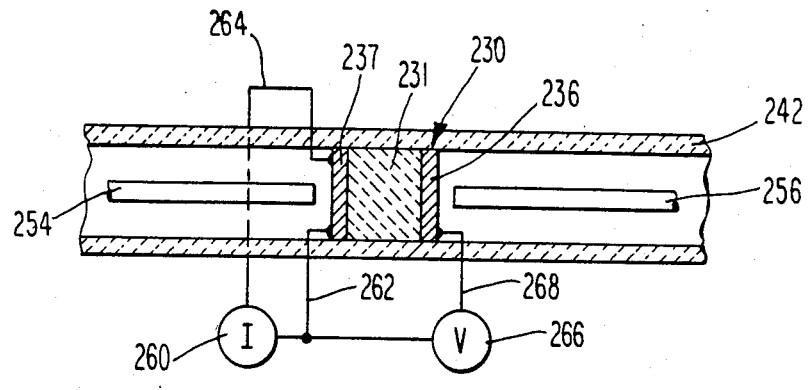
FIG. 8 depicts schematically a second gas detector embodiment incorporating a solid state electrochemical sensing cell with integral heater/electrode and disk shaped solid electrolyte.

While the preferred embodiment of the invention has been described in terms of low temperature gaseous oxygen detector incorporating a close ended tubular electrochemical sensor cell 30, other sensor cell configurations are envisioned to employ the inventive aspects heretofore described. For example, one common configuration for an oxygen or gaseous oxide detector is depicted schematically in FIG. 8 and comprises a solid state electrochemical cell 230 having a disk shaped solid electrolyte 231, a first gas electrode layer 237 on one outer surface of the electrolyte disk 231 and a second gas electrode layer 236 formed on the opposing outer surface of the electrolyte disk 231. Commonly used in an extractive type detector, suitable means such as a non-conductive alumina tube 242 is used to fixably mount the cell 230 and to seal opposing chambers in which a sample gas and a reference gas, respectively, are circulated. The gases are brought into the two chambers to the respective electrode layers 237 and 236 by suitable piping such as quartz or alumina tubes 254 and 256, respectively. For further information regarding the construction of this type of a sensor, see, for example, the U.S. Pat. No. 4,282,078 to Chamberland et al., incorporated by reference herein. One electrode layer 237 is wired by leads 264 and 262 to an alternating electric current source 260 in order that the layer 237 may be used as an integral cell electrode/heater. In addition, the lead 262 branches into a potentiometer 266 or other suitable high impedance device for responding to emf developed between the two electrode layers 237 and 236. Lead 268 completes the circuit between the electrode layers 237 and 236 through the potentiometer 266. The solid electrolyte wafer 231 is envisioned to have circular outer surfaces upon which the electrode layers 237 and 236 are applied. Electrode patterns which have been devised previously for providing substantially large areas of uniform heating for use as stove elements and the like are described in U.S. Pat. Nos. 3,813,520 and 3,848,111, both to Brouneus and hereby incorporated by reference. It is envisioned that these patterns or simple modifications to them may be employed to provide sufficiently large, essentially isothermal active areas in the cell 230 to allow use of the apparatus as an accurate measuring device. Again, the technology has application both to the detection and measurement of oxygen and to the detection and measurement of other gaseous compounds including various gaseous oxides. Again, a solid reference electrode electrochemically suited for the chemical reaction driving the sensor 230 may be employed in place of the gaseous reference electrode layer 236. Also, the two electrode layers 237 and 236 may be circuited through separate alternating current generators and used as combination heater/electrodes.

Figure 9:
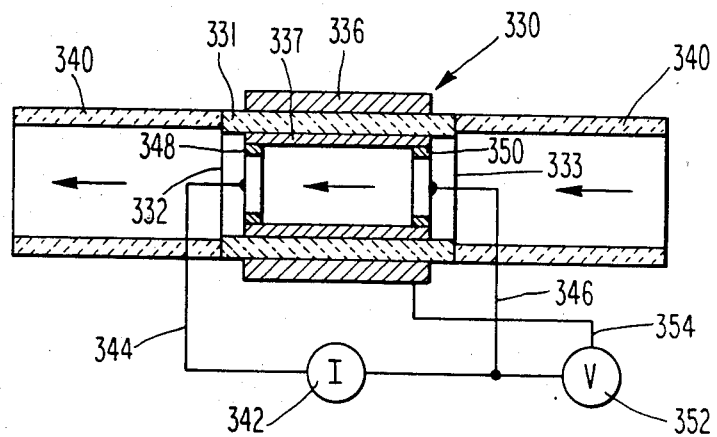
FIG. 9 depicts schematically yet another gas detector apparatus incorporating a solid state electrochemical sensor cell with integral heater/electrode and solid electrolyte with an open tube configuration.

Yet another potential sensor configuration employing an integral heater/electrode which is envisioned is a flow through tube such as is depicted in FIG. 9. An electrochemical sensor cell 330 is provided with a tubular solid electrolyte substrate 331, again of zirconia or other solid electrolyte material suitable for the electrochemical application, having opposing open ends 332 and 333. An inner electrode layer 337 is provided along the inner tubular surface of the substrate 331 while a second electrode layer 336 is applied to the outer surface of the tubular substrate 331. The interior of the tubular substrate 331 would be sealed from its exterior by suitable means such as alumina tubes 340 circulating a reference gas or sample gas mixture through the interior of the cell 330. The cell 330 is again heated by resistively heating one or both of the electrode layers 337 or 336. In the depicted embodiment, a high frequency current source 342 is connected by means of bus leads 344 and 346 to circular terminals 348 and 350 at opposing ends 332 and 333 of the inner electrode layer 337. Again, the inner electrode 337 is electrically connected with the outer electrode 336 across a potentiometer 352 or other high impedance circuit for responding to the emf developed by cell 330.

PROTOTYPE APPARATUS

Figure 10:
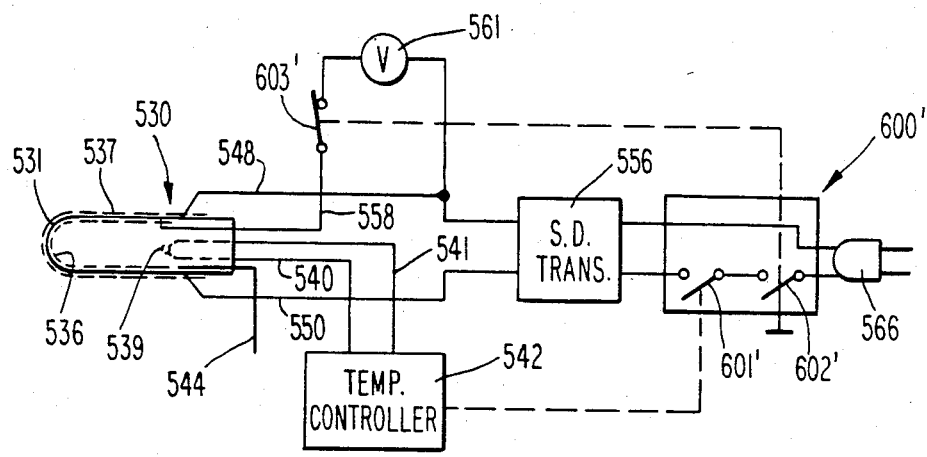
FIG. 10 is a schematic view of a prototype oxygen sensor apparatus.
Figure 11:
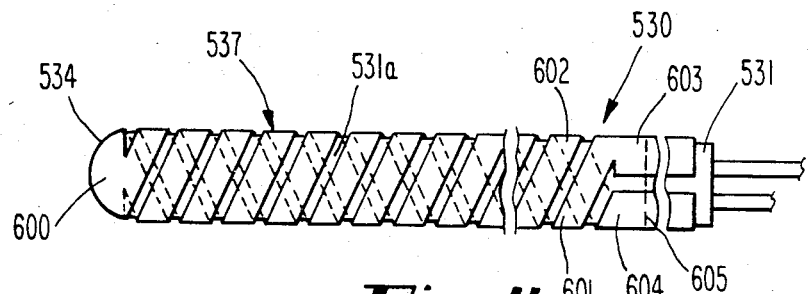
FIG. 11 is a view of a prototype electrochemical cell with integral heater/electrode used in the prototype apparatus of FIG. 10.
Figure 11A:
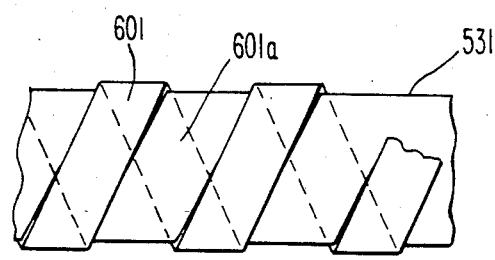
Fig. 11a is an expanded view of a portion of one of two helically wound electrode layer strips forming a part of the integral cell electrode/heater of the prototype cell of FIG. 11.

Depicted diagrammatically in FIG. 10 is an apparatus conceptualizing the manner of operation of the first successful prototype oxygen detection apparatus with integral heater/electrode cell 530. FIGS. 11 and 11a depict the configuration of that prototype cell 530. The apparatus depicted in FIG. 11 includes the sensor cell 530, a thermocouple 539 positioned within the sensor at about the location of the junctions between the leads 548 and 550 and an outer double spiral electrode layer 537 for detecting the maximum temperature of the cell 530. Leads 540 and 541 of the thermocouple 539 are carried to a standard furnace controller 542. A tube 544 carries a sample gas having a known oxygen content to the interior of the cell 530 while the exterior of the cell 530 is exposed to ambient air. The atmospheres inside and outside the cell 530 were isolated from one another by suitable means not shown. Leads 548 and 550 connected a step-down transformer 556 across the integral cell electrode/heater layer 537 on the outer surface of the cell 530. Yet another lead 558 connected an inner electrode layer 536 on the inner surface of the cell 530 and the integral electrode/heater layer 537 on the exterior of the cell 530 across a potentiometer 561. Conventional 60 Hz alternating line current was supplied via plug 566 to the step-down transformer 556. A conceptual switch assembly 600' between the plug 566 and transformer 556 controls the flow of current to the transformer 556. The first switch 601' is operated by the action of the temperature controller 542 while a second switch 602' is manually operated. The operation of switch 602' is linked with that of a switch 603' so that when the alternating current is switched off by switch 602' the potentiometer 561 is activated by switch 603'.

FIG. 11 is a plan view of the prototype electrochemical cell 530. The cell 530 includes a solid yttria stabilized (8% by weight) zirconia substrate solid electrolyte 531 in a tubular configuration similar to that of the solid electrolyte 31 in the cell 30 in FIGS. 1 through 5 having a 6 inch length and $\frac{3}{8}$ inch outer diameter. An outer integral cell electrode/heater layer 537 is formed on the exterior surface of the electrolyte 531 and includes a portion 600 covering the hemispherical tip of the electrolyte 531, a pair of opposing helically extending electrode spirals 601 and 602 about $\frac{1}{8}$ inch wide and extending approximately half the length (3 inches) of the tube and ending in opposing parallel strips 603 and 604, respectively, extending longitudinally for the remainder of the tube length (about 3 inches). The leads 548 and 550 are connected to the longitudinally extending parallel strip portions 603 and 604. The helical nature of the strip 601 is depicted in FIG. 11a. The hidden portion of the strip 601 in FIG. 11 is indicated by the phantom element 601a in FIG. 11a. Narrow spirals 531a of exposed electrolyte separate adjoining spirals 601 and 602 of the electrode layer 537. The solid electrode layer 536 of FIG. 10 is provided entirely across the interior surface of the electrolyte 531 extending from the hemispherically closed end 534 of the electrolyte to a point beyond where the longitudinally extending parallel strip portion 603 and 604 begin. The extent of the inner electrode layer 536 of FIG. 10 is indicated representatively by the dotted line 605 in FIG. 11.

The operation of the apparatus in FIG. 10 was as follows. Switches 601' and 602' were closed allowing the step-down transformer 556 to supply an alternating voltage with a 60 Hz frequency and amplitude of about 5 to 20 volts. This current was passed via the leads 548 and 550 through the outer electrode layer 537. The outer and inner layers 536 and 537 were each formed by three applications of the aforesaid platinum-gold-glass frit material. The sensor 530 was slowly heated (about 300°–400° C. per hour). The controller 542 monitored the temperature of the cell 530 by means of the thermocouple 539 and controlled the on/off operation of the step-down transformer 556 by the switch 601'. When it was desired to measure the emf developed by the cell 530 across the two electrode layers 536 and 537, the alternating current was switched off manually, such as by the switch 602', and the emf developed between layers 536 and 537 measured (in the depicted apparatus by closing the switch 603'). The apparatus generated a two millivolt emf (cell constant C of the Nernst equation) when ambient air was supplied to both electrodes 536 and 537.

Heating of the cell 530 by the depicted outer electrode layer 537 configuration was less optimal that that of the preferred embodiment outer electrode 37 configuration depicted in FIGS. 2 through 4. It was found that when a voltage of sufficient magnitude to heat the cell 530 was circuited through the platinum-gold-glass frit outer electrode layer 537 at the operating temperature of the sensor (nominally 760° C.) shorting of the heater across the electrolyte surface between the helical spiral strip 601 and 602 occurred. Shorting across the electrolyte might occur anywhere along the spiral but once initiated would inevitably travel back toward the junction between the leads 548 and 550 and longitudinally extending parallel strips 603 and 604 of the outer electrode 537 where the voltage difference was greatest. Measurements indicated that when a desired temperature of about 760° C. was eventually produced at the center of the helical windings 601 and 602, the temperature of the electrode at the hemispherical tip 534 was approximately 500° C. and in the vicinity of the junction between the leads 548 and 550 and parallel extending strips 603 and 604 was about 1000° C. Heating of the cell 530 caused the resistivity of the outer electrode layer 537 to rise and the electronic resistivity of the substrate 531 to fall thus forming, in effect, a pair of variable resistors in parallel. The apparatus was made to operate by locating the sensing portion of the thermocouple 539 in the vicinity of the junction between the leads 548 and 550 and the outer electrode layer 537. Once the thermocouple 539 was moved into the vicinity of the junction between the electrode layer 537 and leads 548 and 550 and the voltage adjusted to hold the sensor at about 800° C., the sensor 530 was successfully operated continually for one week without failure. A 60 Hz alternating current of between about 1.5 and 2.0 amps at about 14 volts was used to heat the apparatus. In another experiment, a calcia stabilized zirconia substrate solid electrolyte was substituted for the yttria stabilized electrolyte 531 in the sensor 530. The calcia stabilized zirconia has an electric conductivity an order of magnitude less than that of the yttria stabilized zirconia at the operating temperatures of the cell 530. The calcia stabilized electrolyte cell provided an active zone about one half inch long located about one inch back from the tube tip in the spiral region. However, the calcia stabilized zirconia exhibited susceptibility to electrolysis from the alternating (60 Hz) heater current.

PREFERRED OXYGEN SENSOR INSTRUMENTATION—TEMPERATURE CONTROLLER

An alternate method of applying a setpoint temperature is by known means of ramping the setpoint linearly at a predetermined rate until the oxygen sensor heater element reaches the desired setpoint temperature. The purpose of this technique is to prevent possible damage to the oxygen sensor heater element or oxygen sensor cell due to too large temperature gradients during heat up of the oxygen sensor device.

While various embodiments of the subject invention have been described and modifications thereto suggested, it will be appreciated that other changes and improvements will be apparent to one skilled in the art. The invention is therefore not limited to the disclosure but is set forth in the appended claims.

What is claimed is:

1. An electrochemical cell with integral heater comprising:
   a solid electrolyte having at least a hollow tubular portion with an outer tubular surface and opposing inner tubular surface; and
   an integral cell electrode/heater layer covering substantially all but a pair of opposing, substantially parallel, longitudinally extending strips of the outer tubular surface.

2. The electrochemical cell of claim 1 wherein said electrolyte tubular portion has a substantially circular cross-section with a substantially uniform cross-sectional thickness and said layer has a substantially uniform composition and thickness along at least a major proportion of the outer tubular surface.

3. The electrochemical cell of claim 1 wherein said solid electrolyte further comprises a hollow, substantially hemispherical portion integrally formed with one end of the tubular portion, the hemispherical portion having a convex outer surface and an opposing concave inner surface and wherein the layer covers at least a major proportion of the convex outer surface.

4. The electrochemical cell of claim 3 wherein said strips extend from an end of said layer proximal a remaining open end of the tubular portion of the electrolyte to the hemispherical portion of the electrolyte and wherein said integral layer covers the entire convex outer surface.

5. The electrochemical cell of claim 3 wherein the opposing parallel strips of exposed electrolyte extend from an end of the layer proximal a remaining open end of the tubular portion of the electrolyte and divide said layer into two portions, the two layer portions beginning at the end of the layer proximal the remaining open end of the tubular portion of the electrolyte and joining at the hemispherical portion end of the tubular electrolyte portion to form a single continuous layer, and said layer having a maximum total resistance of about one-half ohm or less at room temperature.

6. The electrochemical cell of claim 1 further comprising a second electrode layer contacting said inner tubular surface of the electrolyte opposite said integral cell electrode/heater layer and extending along at least a portion of the length of the tubular portion exposed by the two opposing strips.

7. The electrochemical cell of claim 6 wherein the two electrode layers are each formed from a material comprising a major proportion by weight of platinum and are porous to gaseous oxygen; and wherein said solid electrolyte is formed from a material comprising a major proportion by weight of zirconia.

8. An electrochemical apparatus comprising:
   an electrochemical cell including an electrolyte, a first integral cell electrode and a second cell electrode means and adapted for developing an emf between the first integral cell electrode and the second cell electrode during operation of the cell;
   generation means for supplying radio frequency alternating current; and
   circuit means including a pair of leads each having an end coupled with a different part of said first integral cell electrode and an opposing end coupled with said generation means connecting said generation means in a circuit through said cell across said first integral cell electrode for resistively heating at least said first integral cell electrode portion of the cell with said radio frequency alternating electric current.

9. The electrochemical apparatus of claim 8 wherein said alternating electric current has a frequency of alternation sufficiently high that the emf developed by the electrochemical cell is substantially unaffected by any further increase of the frequency of alternation of said alternating current.

10. The electrochemical apparatus of claim 8 wherein the frequency of the alternating current is between about 3,000 and 300,000 hertz.

11. The electrochemical apparatus of claim 10 wherein the frequency of the alternating current is further between about 30,000 and 100,000 hertz.

12. The electrochemical apparatus of claim 8 further comprising:
temperature sensing means for generating a signal related to the temperature of the electrochemical cell; and
control means responsive to the temperature signal for controlling the power level of the alternating current supplied by said generation means through said cell.

13. The electrochemical apparatus of claim 12 wherein said control means comprises means for automatically switching the alternating current on and off.

14. The electrochemical apparatus of claim 12 wherein said control means comprises:
a radio frequency oscillator; and
means for regularly activating said radio frequency oscillator for varying periods of time.

15. The apparatus of of claim 14 wherein said means for regularly activating comprises:
amplifier means responsive to said temperature signal for outputting a signal related to the difference between a temperature indicated by said temperature signal and a predetermined temperature; and
pulse width modulated oscillator means responsive to said amplifier means output signal for outputting a signal of varying duration at regular time intervals to said radio frequency oscillator.

16. The electrochemical apparatus of claim 15 wherein said radio frequency oscillator outputs a signal of no more than one polarity and further comprising current generator means connected across said pair of leads and responsive to said radio frequency oscillator output signal for generating an alternating current circuiting through said pair of leads with a frequency of alternation equal to the radio frequency of said reference oscillator output signal.

17. The apparatus of claim 8 wherein:
said electrolyte is solid and includes a hollow, tubular portion with an outer tubular surface and an opposing inner tubular surface and an open tubular end; and
said first integral cell electrode comprises:
an electrically conductive layer covering a major proportion of the outer tubular surface of the electrolyte; and
the cell further comprises:
a pair of strips of exposed electrolyte outer tubular surface extending along at least part of the tubular portion of the electrolyte, the strips dividing the electrode layer into two portions from an end of the layer proximal the open tubular end of the electrolyte, the electrode layer being circumferentially continuous about the electrode outer surface at an opposing end of the electrolyte; and
each lead extends from an end of a different one of the two portions of the electrode layer to the generation means whereby substantially all of the electrode layer is connected in a circuit with the generation means.

18. The electrochemical apparatus of claim 17 where the resistance of the electrode layer between the two lead contact points is about one-half ohm or less at room temperature.

19. An electrochemical apparatus responding to a predetermined gaseous substance in a sample gas comprising:
an electrochemical cell, the cell comprising:
a solid electrolyte exhibiting an increased conductivity to ions of the predetermined gaseous substance when heated,
first electrode means contacting the surface of the solid electrolyte at a first location for forming a gas electrode with the sample gas and the electrolyte and
second electrode means contacting the surface of the solid electrolyte at a second location for generating a known, predetermined potential with said solid electrolyte,
the electrochemical cell developing an emf between the two electrode means related to the concentration of the predetermined gaseous substance in the sample gas at the first electrode means; and
electric current source means connected in an electrical circuit across only an electrode means portion of the cell and adapted for passing a radio frequency electric alternating current through only said electrode means portion of the cell.

20. The electrochemical apparatus of claim 19 further comprising a pair of electrically conductive leads extending from different portions of one of said first and second electrode means to the electric current source means.

21. The electrochemical apparatus of claim 20 wherein the solid electrolyte includes a hollow tubular portion with an outer tube surface and an opposing inner tube surface; wherein the one electrode means includes an electrically conductive layer porous to the gaseous substance and covering substantially all but a pair of opposing longitudinally extending strips of the outer tube surface dividing the layer into two sections extending along the tube portion of the electrolyte; and wherein each of said leads extends from a different one of said two sections.

22. The electrochemical apparatus of claim 21 wherein said tubular portion is substantially circular in cross-section with a substantially uniform cross-sectional thickness and said layer has a substantially uniform composition and thickness along said outer tube surface.

23. The electrochemical apparatus of claim 21 wherein said electrolyte further includes a hollow, substantially hemispherical portion integrally closing one end of the tubular portion and having an outer convex surface and an opposing inner concave surface; and wherein the layer is circumferentially continuous at the outer convex surface.

24. The electrochemical apparatus of claim 23 wherein said opposing longitudinally extending strips are substantially parallel, divide the layer into sections of substantially equal size and extend from an end of said layer proximal an opposing open end of the tube portion to said hemispherical portion of said solid electrolyte; and wherein said layer covers the entire outer convex surface.

25. The electrochemical apparatus of claim 21 wherein said one electrode means further has a reduced resistivity in the vicinity of each of the contacting conductive leads.

26. The electrochemical apparatus of claim 25 wherein said one electrode means further includes a pair of metal foil pads each pad being located between the electrode layer and an end of a different one of the two conductive leads.

27. The electrochemical apparatus of claim 21 wherein the remaining electrode means comprises a second, gas porous, electrically conductive layer circumferentially covering a portion of the inner tube surface over an area extending along at least a portion of the tube surface exposed by the opposing strips.

28. The electrochemical apparatus of claim 27 wherein the two electrode layers are each formed from a material comprising a major proportion by weight of platinum and said solid electrolyte is formed from a material comprising a major proportion by weight of zironia.

29. An improved method of heating an electrochemical cell formed by an electrolyte and a pair of electrode means separately contacting the electrolyte for developing an emf therebetween comprising the steps of:
generating an alternating electric current having a radio frequency level of alternation; and
passing the alternating electric current through at least one of said pair of electrode means while passing no more than a negligible portion of said alternating electric current through said electrolyte.

30. The improved method of claim 29 wherein the generating step further comprises the step of:
generating an alternating current with a frequency of alternation sufficiently high as to eliminate any offset in the manitude of the emf developed by the electrochemical cell caused by the frequency of the alternating current.

31. The improved method of claim 29 wherein the passing step further comprises the step of passing the radio frequency alternating current through only one of the two cell electrode means.

32. The improved method of claim 29 wherein said generating step further comprises generating an alternating electric current with a frequency of alternation of between about 30,000 and 100,000 hertz.

33. The improved method of claim 29 further comprising the step of sensing the temperature of the cell and wherein said step of generating further comprises varying the power of the alternating electric current passed through the cell in response to said sensing step.

34. An improved method of heating an electrochemical cell, the cell comprising an electrolyte and a pair of cell electrodes contacting the electrolyte, the method comprising the step of:
resistively heating at least one of the two cell electrodes while no more than negligibly resistively heating the electrolyte.

35. The improved method of claim 34 wherein said resistive heating step further comprises the steps of:
generating an electric current; and
passing said electric current through at least one cell electrode means while passing no more than a negligibl portion of said electric current through the electrolyte.

36. The improved method of claim 35 wherein said generating step further comprises the step of generating an alternating electric current having a frequency of between about 3,000 and 300,000 hertz.

37. The improved method of claim 34 wherein the electrolyte is a solid, wherein each of said two cell electrode means contacts one of a pair of opposing surfaces of he electrolyte and wherein the resistive heating step further comprises the steps of:
warming a zone of the electrolyte to a maximum temperature with said resistively heated one electrode means, the zone extending through the electrolyte between the two electrode means and covering an area of at least several square centimeters; and
thereafter maintaining the temperature of the electrolyte in the zone within about 10° C. or less of said maximum temperature by resistively heating said one electrode means.

38. The improved method of claim 34 wherein the electrolyte is a solid and at least one of the electrodes further comprises an electrically conductive layer covering at least a portion of an outer surface of the solid electrolyte and the resistive heating step further comprises the step of:
passing a substantially uniform electric current power density through a major proportion of the electrically conductive layer.

39. An improved method of operating a device for generating a signal related to a concentration of a particular gas in a sample gas, said device comprising an electrochemical cell having an electrolyte heated to an elevated temperature for operation, a first electrode means exposed to the sample gas and a second electrode means developing an emf with the first electrode means, sample gas and electrochemical cell having a magnitude related to the concentration of the particular gas in the sample gas, comprising the steps of:
generating radio frequency alternating current; and
passing said alternating electric current through at least a portion of one of the electrode means contacting the electrolyte for resistively heating only the one electrode means portion of the cell with said current; and
generating an emf with the cell during said current generating and passing steps having a magnitude releated to the concentration of the particular gas in the sample gas.

40. The improved method of claim 39 wherein said step of generating further comprises a step of:
generating an alternating current having a frequency of alternation sufficiently high that the magnitude of the emf developed by the electrochemical cell is substantially uneffected by further increase in said frequency of said alternating electric current.

41. The improved method of claim 40 wherein said electrolytic cell includes a zirconia electrolyte, said particular gas is oxygen and said electrolyte is warmed to a temperature of at least about 600° C.

42. The improved method of claim 40 further comprising during said passing step the step of:
simultaneously generating a signal related to the magnitude of the emf being developed by the cell for indicating the concentration of the particular gas in the sample gas.

43. The improved method of claim 42 further comprising during the current generating and passing steps the step of simultaneously sensing the temperature of the electrochemical cell; and said generating step further comprises the step of varying the power of the alternating electric current in response to said temperature sensing step.

44. The improved method of claim 43 wherein said electrolyte is solid and said one electrode means comprises a solid, electrically conductive layer contacting at least a portion of a surface of the solid electrolyte and said passing step further comprises the step of:
passing said alternating electric current through the layer while passing no more than a negligible portion of the alternating electric current through said solid electrolyte.

45. The improved method claim 42 wherein said electrolytic cell includes a zirconia electrolyte, said particular gas is oxygen and said electrolyte is warmed to a temperature of at least about 600° C.

46. The improved method of claim 39 wherein said electrolyte is solid and said one electrode means includes a solid, electrically conductive layer contacting at least a portion of a surface of the solid electrolyte and said passing step further comprises the step of:
  passing said alternating electric current through the layer while passing no more than a negligible portion of the alternating electric current through said solid electrolyte.

47. An electrochemical cell comprising:
  an electrolyte;
  integral cell electrode/heater means contacting the electrolyte and adapted for heating at least a portion of the electrolyte to an elevated temperature for ionic conduction operation; and
  a pair of lead means each extending from a different location on the integral cell electrode/heater means for coupling said integral cell electrode/heater means in a circuit across an electric current source; and
  a second cell electrode means separately contacting the electrolyte and adapted for developing an ionic conduction across the heated electrolyte and a related emf with the integral cell electrode/heater.

48. The cell of claim 47 wherein said electrolyte is a solid at said elevated temperature and has a surface and said integral cell electrode/heater means comprises an electrically conductive layer contacting at least a portion of the surface of the solid electrolyte.

49. The cell of claim 48 wherein the electrolyte has a hollow tubular form, an outer surface and an opposing inner surface and said layer covers a major proportion of said outer surface.

50. The cell of claim 49 wherein said hollow tubular form of said electrolyte has an open end and a closed end and wherein said layer includes a circumferentially continuous portion at the closed end and a pair of separate legs extending from the circumferentially continuous portion to an end of said layer proximal said open end of the electrolyte.

51. The cell of claim 50 wherein said integral cell electrode/heater means further comprises a pair of metal foil pads each attached to a separate one of the pair of legs of the layer so as to effectively reduce the surface resistivity of the integral cell electrode/heater means at said pads.

52. The cell of claim 49 wherein said layer covers all of said hollow tubular form of the electrolyte but a pair of stripes of exposed electrolyte surface, extending along the hollow tubular form and dividing part of said layer extending along the hollow tubular form into a pair of legs.

53. The cell of claim 48 wherein the layer is gas porous.

54. The cell of claim 48 wherein said layer is formed from a material comprising platinum.

55. The cell of claim 54 wherein a chemical bond is formed between at least a portion of said layer and said solid electrolyte.

56. The cell of claim 47 in a combination further comprising:
  electric current source means electrically connected in a circuit across said pair of lead means and circuiting an alternating electric current across said integral cell electrode/heater means through said pair of leads means.

57. The cell of claim 47 in a combination further comprising:
  electric current source means electrically connected in a circuit across the integral cell electrode/heater means for circuiting an electric current through at least a portion of the integral cell electrode/heater means.

58. The combination of claim 57 wherein said electric current source means comprises:
  switch means for controlling the electric current circuited through the integral cell electrode/heater means.

59. The combination of claim 57 wherein said electrolyte is a solid at said elevated temperature and has a surface and said integral cell electrode/heater means comprises an electrically conductive layer contacting a portion of the surface of the solid electrolyte.

60. An electrochemical apparatus responding to a predetermined gaseous substance in a sample gas comprising:
  an electrochemical cell, the cell comprising:
    a solid electrolyte exhibiting a conductivity to ions of the predetermined gaseous substance when heated above room temperature,
    first electrode means contacting the surface of the solid electrolyte at a first location for forming a gas electrode with said sample gas and the electrolyte, and
    second electrode means contacting a surface of the solid electrode at a second location for forming a reference electrode generating a known, predetermined ionic potential with said solid electrolyte; and
  an electric current source means electrically connected across one of the two electrode means for resistively heating at least a portion of the one electrode means sufficiently for the cell to develop an ionic emf between the two electrode means related to the concentration of the predetermined gaseous substance in the sample gas.

61. The electrochemical apparatus of claim 60 wherein said one electrode means comprises an electrically conductive layer contacting the solid electrolyte.

62. The electrochemical apparatus of claim 61 wherein the layer is chemically bonded to the solid electrolyte.

63. The electrochemical apparatus of claim 61 wherein said electrolyte is a material comprising a major proportion by weight of zirconia and said layer is a material comprising a major proportion by weight of platinum and a minor proportion by weight of a substance chemically bonding to the zirconia.

64. The electrochemical apparatus of claim 61 wherein the solid electrolyte has a hollow tubular form with an outer surface and an opposing inner surface and said layer covers a major proportion of said outer layer.

65. The electrochemical apparatus of claim 64 wherein the one electrode means layer is gas porous and the remaining electrode means comprises a second gas porous, electrically conductive layer contacting the inner surface opposite the one electrode layer.

66. The electrochemical apparatus of claim 64 wherein said layer is circumferentially continuous at one end of the tubular portion of the electrolyte and divided into a pair of separate, substantially equal legs along the remainder of the tubular portion of the electrolyte by a pair of exposed strips of electrolyte outer tubular surface; and further comprising:

a pair of leads each connecting a separate one of the pair of legs with said electric current source means.

67. The electrochemical apparatus of claim 66 wherein said remaining electrode means comprises a second gas porous, electrically conductive layer contacting the inner tubular surface opposite at least a portion of said outer layer between said one end of the electrolyte and said leads contacting the outer layer.

68. The electrochemical apparatus of claim 67 wherein said electric current source means comprises a step down transformer connected by said leads across said layer.

69. The electrochemical apparatus of claim 57 wherein said identified compound is oxygen and said electrolyte is formed from a material comprising stabilized zirconia.

70. The electrochemical apparatus of claim 57 wherein the electric current source means circuits an alternating electric current through at least a portion of the one electrode means.

71. The electrochemical apparatus of claim 60 further comprising:

a pair of leads extending from different parts of the one electrode means across said electric current source means.

72. A method of heating an electrolyte of an electrochemical cell to an elevated cell ionic conduction operating temperature, the electrochemical cell being formed by the electrolyte, a first cell electrode and a second cell electrode, the method comprising the step of:

circuiting an alternating electric current through only a cell electrode portion of the cell.

73. The method of claim 72 wherein said alternating electric current circuited through said cell has a 60 hertz frequency of alternation.

74. A method of heating an electrolyte of an electrochemical cell to an elevated cell ionic conduction operating temperature, the electrochemical cell being formed by the electrolyte, a first cell electrode and a second cell electrode, the method comprising the step of:

resistively heating at least a portion of one of the two cell electrodes contacting the electrolyte to at least said elevated cell ionic conduction operating temperature.

75. The method of claim 74 wherein the resistive heating step comprises the step of circuiting an alternating electric current through at least a portion of only the one of the two cell electrodes.

76. The method of claim 75 further comprising a second subsequent resistive heating step of passing an alternating electric current through at least said portion of the one cell electrode and through at least part of the solid electrolyte.

77. The method of claim 74 wherein said electrolyte is a solid and ionically conductive at said operating temperature and said method further comprises the step of:

resistively heating at least a portion of the solid electrolyte and said portion of the one electrode after said cell has been heated by said one electrode.

78. A method of operating an apparatus for sensing a particular gaseous substance, the apparatus comprising an electrochemical cell heated to an elevated temperature for ionic conduction operation and circuit means for responding to an ionic emf developed by the electrochemical cell, the electrochemical cell comprising a solid electrolyte exhibiting increased conductivity to ions of the gaseous substance when heated to the elevated temperature, a first cell electrode contacting the electrolyte and exposed to a sample gas and a second cell electrode also contacting the electrolyte at a separate location and generating a predetermined potential, the electrochemical cell developing an ionic emf between the two cell electrodes related to the concentration of the particular gaseous substance in the sample gas, comprising the steps of:

resistively heating at least a portion of one of the two electrodes to said elevated temperature; and measuring the ionic emf developed between the two cell electrodes after the electrolyte has been heated to said elevated temperature.

79. The method of claim 78 further comprising the step of terminating the resistive heating step before the measuring step.

80. The method of claim 79 wherein the one electrode is again resistively heated after said measuring step and before a second, similar measuring step.

81. The method of claim 78 further comprising during the step of resistively heating at least a portion of the one electrode, the step of simultaneously resistively heating a portion of the solid electrolyte.

82. The method of claim 81 further comprising the steps of terminating the two resistive heating steps before the measuring step.

83. The method of claim 78 wherein the resistive heating step comprises the step of circuiting an alternating electric current through only one of the two cell electrodes.

84. The method of claim 83 further comprising the step of circuiting a portion of the alternating electric current through a portion of the solid electrolyte.

85. The method of claim 83 further comprising the steps of:

measuring the temperature of the cell; and
terminating the alternating electric current in response to the temperature measuring step.

86. The method of claim 85 further comprising the step of initiating the ionic emf measuring step in response to said terminating step.

87. A method of operating an apparatus for sensing a particular gaseous substance, the apparatus comprising an electrochemical cell heated to an elevated temperature for ionic conduction operation and circuit means for responding to an ionic emf developed by the electrochemical cell, the electrochemical cell comprising a solid electrolyte exhibiting increased conductivity to ions of the gaseous substance when heated to the elevated temperature, a first cell electrode contacting the electrolyte and exposed to a sample gas and a second cell electrode also contacting the electrolyte at a separate location and generating a predetermined potential, the electrochemical cell developing an ionic emf between the two cell electrodes related to the concentration of the particular gaseous substance in the sample gas, comprising the steps of:

circuiting an alternating electric current through only a cell electrode portion of the cell sufficient to heat said cell; and measuring the emf developed between the two cell electrodes after the electrolyte has been heated to said elevated temperature.

88. An improved method of operating a device for generating a signal related to the concentration of a particular gas in a sample gas, said device comprising an electrochemical cell heated for ionic conduction operation, exposed to the sample gas and developing an ionic emf having a magnitude related to the concentration of the particular gas in the sample gas comprising the steps of:
  generating an alternating electric current in a substantially constant voltage band;
  passing said alternating current through at least a portion of the electrochemical cell for resistively heating the cell; and
  cyclicly switching the alternating electric current off during said generating and passing steps for irregular portions of a series of consecutive, predetermined cycle intervals.

89. The improved method of claim 88 further comprising during said cyclicly switching step, the steps of:
  sensing the ionic emf developed by the electrochemical cell; and
  generating a signal related to the magnitude of the ionic emf being developed by the cell for indicating the concentration of the particular gas in the sample gas.

90. An electrochemical cell with integral heater comprising:
  a solid electrolyte;
  an integral cell electrode/heater means comprising an electrically conductive layer contacting and covering a portion of the solid electrolyte; and
  an electric current source means electrically connected across only the electrode/heater means for resistively heating at least a portion of the electrode/heater means.

* * * * *